(12) United States Patent
Kuramoto

(10) Patent No.: US 11,328,415 B2
(45) Date of Patent: May 10, 2022

(54) MEDICAL IMAGE PROCESSING DEVICE, ENDOSCOPE SYSTEM, AND METHOD OF OPERATING MEDICAL IMAGE PROCESSING DEVICE

(71) Applicant: FUJIFILM Corporation, Tokyo (JP)

(72) Inventor: Masayuki Kuramoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 59 days.

(21) Appl. No.: 16/714,377

(22) Filed: Dec. 13, 2019

(65) Prior Publication Data

US 2020/0118268 A1 Apr. 16, 2020

Related U.S. Application Data

(63) Continuation of application No. PCT/JP2018/021573, filed on Jun. 5, 2018.

(30) Foreign Application Priority Data

Jun. 15, 2017 (JP) .............................. JP2017-117437

(51) Int. Cl.
    *G06T 7/00* (2017.01)
(52) U.S. Cl.
    CPC .. *G06T 7/0012* (2013.01); *G06T 2207/10024* (2013.01); *G06T 2207/10068* (2013.01); *G06T 2207/20208* (2013.01)
(58) Field of Classification Search
    None
    See application file for complete search history.

(56) References Cited

U.S. PATENT DOCUMENTS

| 6,351,558 | B1 | 2/2002 | Kuwata |
| 7,613,335 | B2* | 11/2009 | McLennan ........... G06K 9/4652 |
| | | | 382/128 |
| 9,430,833 | B2* | 8/2016 | Ikemoto ............. A61B 1/00009 |
| 2007/0147541 | A1 | 6/2007 | Saito |

(Continued)

FOREIGN PATENT DOCUMENTS

| CN | 101349961 A | 1/2009 |
| CN | 102197985 A | 9/2011 |

(Continued)

OTHER PUBLICATIONS

International Search Report issued in PCT/JP2018/021573; dated Aug. 7, 2018.

(Continued)

*Primary Examiner* — Vu Le
*Assistant Examiner* — Courtney Joan Nelson
(74) *Attorney, Agent, or Firm* — Studebaker & Brackett PC

(57) ABSTRACT

As saturation enhancement processing, first saturation enhancement processing or second saturation enhancement processing different from the first saturation enhancement processing is executed. A high saturation range Ry(rc)Ry(r2) after the second saturation enhancement processing is greater than a high saturation range Rx(rc)Rx(r2) after the first saturation enhancement processing. A value Ry(r) included in the high saturation range Ry(rc)Ry(r2) after the second saturation enhancement processing is smaller than a value Rx(r) included in the high saturation range Rx(rc)Rx(r2) after the first saturation enhancement processing.

12 Claims, 26 Drawing Sheets

(56) References Cited

U.S. PATENT DOCUMENTS

| | | | |
|---|---|---|---|
| 2008/0090198 A1 | 4/2008 | Liang et al. | |
| 2011/0237882 A1 | 9/2011 | Saito | |
| 2014/0031628 A1 | 1/2014 | Kaku | |
| 2014/0187932 A1 | 7/2014 | Li et al. | |
| 2014/0320620 A1 | 10/2014 | Ikemoto et al. | |
| 2015/0193929 A1* | 7/2015 | Ikemoto | A61B 5/061 382/128 |
| 2015/0216460 A1* | 8/2015 | Shigeta | A61B 1/05 600/339 |
| 2015/0374263 A1 | 12/2015 | Kuramoto et al. | |
| 2016/0007829 A1 | 1/2016 | Chun | |
| 2016/0015505 A1 | 1/2016 | Johnson et al. | |
| 2016/0029925 A1* | 2/2016 | Kuramoto | A61B 1/00009 348/65 |
| 2016/0093067 A1* | 3/2016 | Kuramoto | G06K 9/6215 382/128 |
| 2016/0140713 A1 | 5/2016 | Martin | |
| 2016/0239965 A1 | 8/2016 | Kuramoto | |

FOREIGN PATENT DOCUMENTS

| | | |
|---|---|---|
| CN | 103142325 A | 6/2013 |
| CN | 103426373 A | 12/2013 |
| CN | 103892859 A | 7/2014 |
| CN | 104272134 A | 1/2015 |
| CN | 105212885 A | 1/2016 |
| CN | 105310633 A | 2/2016 |
| CN | 105379264 A | 3/2016 |
| CN | 105407835 A | 3/2016 |
| CN | 105455773 A | 4/2016 |
| CN | 105705075 A | 6/2016 |
| CN | 105796044 A | 7/2016 |
| CN | 106558031 A | 4/2017 |
| EP | 2 368 487 A1 | 9/2011 |
| EP | 2 665 100 A2 | 11/2013 |
| JP | 2002-281327 A | 9/2002 |
| JP | 2003-50997 A | 2/2003 |
| JP | 2005-286995 A | 10/2005 |
| JP | 2009-226095 A | 10/2009 |
| JP | 2013-058920 A | 3/2013 |
| JP | 2014-023591 A | 2/2014 |
| JP | 5568489 B2 | 8/2014 |
| JP | 2014-213094 A | 11/2014 |
| JP | 5631764 B2 | 11/2014 |
| JP | 5647752 B1 | 1/2015 |
| JP | 2015-146924 A | 8/2015 |
| JP | 2016-034405 A | 3/2016 |
| JP | 2016-067709 A | 5/2016 |
| WO | 2013/128301 A2 | 9/2013 |
| WO | 2014/013778 A1 | 1/2014 |
| WO | 2015/064435 A1 | 5/2015 |

OTHER PUBLICATIONS

International Preliminary Report on Patentability and Written Opinion issued in PCT/JP2018/021573; dated Dec. 17, 2019.

An Office Action; "Notice of Reasons for Refusal," mailed by the Japanese Patent Office dated Jan. 19, 2021, which corresponds to Japanese Patent Application No. 2019-525339 and is related to U.S. Appl. No. 16/714,377; with English language translation.

An Office Action; "Notice of Reasons for Refusal," mailed by the Japanese Patent Office dated Aug. 24, 2021, which corresponds to Japanese Patent Application No. 2019-525339 and is related to U.S. Patent Application No. 16/714,377; with English language translation.

An Office Action mailed by China National Intellectual Property Administration dated Sep. 18, 2021, which corresponds to Chinese Patent Application No. 201880039884.8 and is related to U.S. Appl. No. 16/714,377 with English language translation.

* cited by examiner

FIG. 15
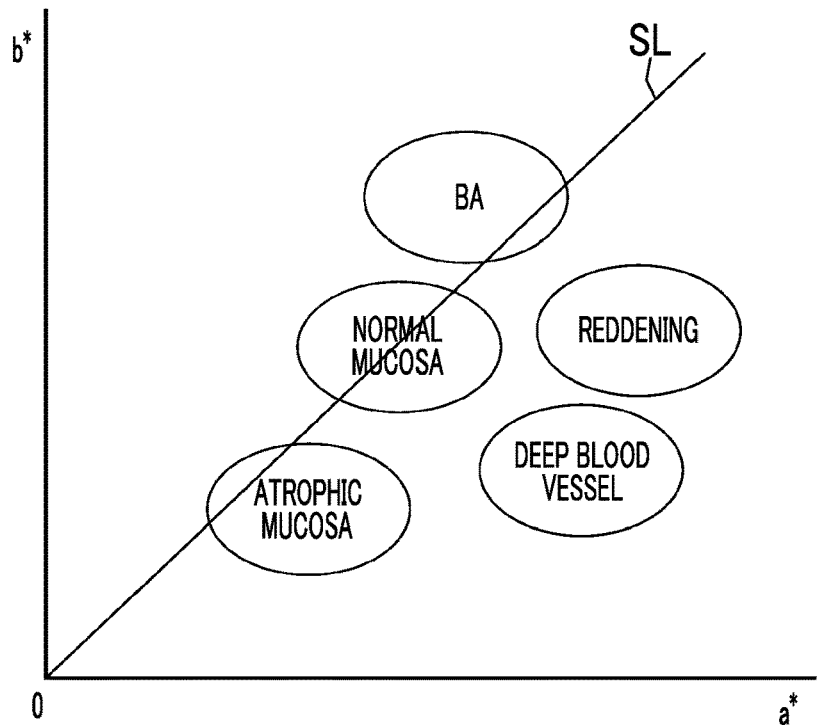
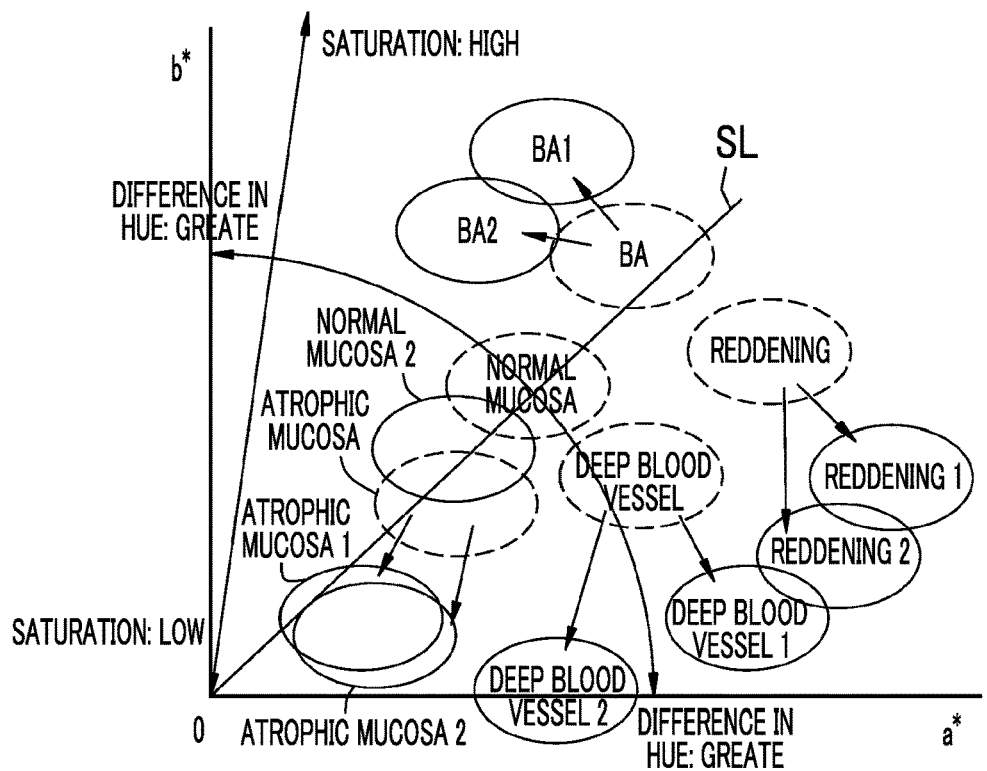

FIG. 17

```
SETTING MENU
(SPECIAL OBSERVATION MODE)

OBSERVATION MODE          DISPLAY MODE

☐ C1: INFLAMMATION        ☐ TWO-SCREEN
   EVALUATION MODE

☐ C2: UC SCREENING MODE

☐ C3: NORMAL MODE
```

MEDICAL IMAGE PROCESSING DEVICE, ENDOSCOPE SYSTEM, AND METHOD OF OPERATING MEDICAL IMAGE PROCESSING DEVICE

CROSS-REFERENCE TO RELATED APPLICATIONS

This application is a Continuation of PCT International Application No. PCT/JP2018/021573 filed on 5 Jun. 2018, which claims priority under 35 U.S.C § 119(a) to Japanese Patent Application No. 2017-117437 filed on 15 Jun. 2017. The above application is hereby expressly incorporated by reference, in its entirety, into the present application.

BACKGROUND OF THE INVENTION

1. Field of the Invention

The present invention relates to a medical image processing device that processes a medical image obtained by imaging an observation target in a subject, an endoscope system, and a method of operating a medical image processing device.

2. Description of the Related Art

In a recent medical field, an endoscope system comprising a light source device, an endoscope, and a processor device has been widely used. In this endoscope system, an observation target is irradiated with illumination light from the endoscope, and an image of the observation target is displayed on a monitor based on an RGB image signal obtained by imaging the observation target being irradiated with illumination light with an imaging element of the endoscope.

In endoscope observation, imaging conditions, such as a distance to the observation target or light emission conditions of illumination light, may be appropriately changed according to the purpose of diagnosis. However, since an operation to change the imaging conditions in this way imposes a burden on a user, as described in JP5631764B or JP5568489B, observation modes or light emission conditions of illumination light may be automatically switched.

In recent years, a lesion part of a stomach, such as a gastric cancer, is detected from a state of atrophic gastritis using an endoscope. In order to facilitate diagnosis of atrophic gastritis, in JP5647752B (corresponding to US2016/007829A1), processing for enhancing the difference in color between a normal part and an abnormal part, such as atrophic gastritis, is executed, thereby facilitating ascertaining a state of a mucosa atrophied due to atrophic gastritis.

SUMMARY OF THE INVENTION

As described above, in addition to detection of the lesion part of the stomach, such as atrophic gastritis, a lesion part of a colon may be detected using the endoscope. In detecting ulcerative colitis as the lesion part of the colon, in addition to the degree of inflammation of a mucosa, the degree of seeing-through of a deep blood vessel in a deep layer of an inflamed mucosa is also an important index. For example, there is a case where the presence or absence of ulcerative colitis is determined based on blocking of the deep blood vessel, or the like.

In contrast, in order to improve the visibility of the deep blood vessel, as described in JP5647752B, it is considered that the processing for enhancing the difference in color between a normal part and an abnormal part is executed. However, in a case where the processing of JP5647752B is executed on an image obtained by the observation of the colon as it is, the portion of the deep blood vessel is enhanced with high saturation, and the redness of the deep blood vessel becomes intense. In this case, the visibility of the deep blood vessel is deteriorated, and for example, the blocking of the deep blood vessel is hardly detected. In follow-up observation of a patient who suffers from ulcerative colitis, in a case where the processing of JP5647752B is executed as it is, since a user continues to view an image with high saturation and there is a concern that the user undergoes eyestrain, the processing may not be suitable for long-term inspection.

An object of the invention is to provide a medical image processing device, an endoscope system, and a method of operating a medical image processing device capable of extending a range of high saturation to increase visibility of an observation target while suppressing saturation enhancement of the observation target included in the range of high saturation in a case where processing for enhancing the difference in saturation between a normal part and an abnormal part is executed.

A medical image processing device of the invention comprises a processor configured to function as an image signal input unit, a color information acquisition unit, and a saturation enhancement processing unit. The image signal input unit receives a color image signal as input. The color information acquisition unit acquires a plurality of pieces of color information from the color image signal. The saturation enhancement processing unit executes saturation enhancement processing on a high saturation range on a high saturation side with respect to at least a specific saturation boundary line in a feature space formed from the plurality of pieces of color information to make differences in saturation among a plurality of observation target ranges distributed as an observation target large. The saturation enhancement processing unit executes, as the saturation enhancement processing, first saturation enhancement processing or second saturation enhancement processing different from the first saturation enhancement processing. The high saturation range after the second saturation enhancement processing is greater than the high saturation range after the first saturation enhancement processing, and a value included in the high saturation range after the second saturation enhancement processing is smaller than a value included in the high saturation range after the first saturation enhancement processing.

It is preferable that the processor is further configured to function as a hue enhancement processing unit that executes hue enhancement processing on a specific hue range in a specific hue direction with respect to at least a specific hue boundary line in the feature space to make differences in hue among a plurality of observation target ranges distributed as an observation target large, and the hue enhancement processing unit executes, as the hue enhancement processing, first hue enhancement processing or second hue enhancement processing with the difference in hue greater than the first hue enhancement processing.

It is preferable that the processor is further configured to function as a mode controller that performs switching between a first mode for obtaining a first saturation enhanced image from a color image signal subjected to the first saturation enhancement processing and a second mode for obtaining a second saturation enhanced image from a color image signal subjected to the second saturation enhancement processing.

It is preferable that the mode controller automatically performs switching between the first mode and the second mode according to observation target information obtained by digitizing a state of the observation target. It is preferable that the observation target information corresponds to a value obtained based on the color information of any one observation target range of the plurality of observation target ranges. It is preferable that the observation target information corresponds to a value obtained based on an angle of coordinates of any one observation target range of the plurality of observation target ranges with respect to the specific hue boundary line.

It is preferable that the observation target information corresponds to a value obtained based on a distance between two observation target ranges among the plurality of observation target ranges. It is preferable that the observation target information is an area ratio indicating an occupying ratio of pixels of any one observation target range of the plurality of observation target ranges among pixels of the color image signal. It is preferable that the observation target information is a degree of inflammation obtained by digitizing an inflamed state of the observation target. It is preferable that the color image signal is obtained by imaging an observation target illuminated with illumination light including violet light.

An endoscope system of the invention comprises the medical image processing device of the invention described above and a display unit. The display unit displays at least one image of a first saturation enhanced image obtained from a color image signal subjected to the first saturation enhancement processing, a second saturation enhanced image obtained from a color image signal subjected to the second saturation enhancement processing, or a normal image obtained from a color image signal not subjected to the first saturation enhancement processing and the second saturation enhancement processing.

A method of operating a medical image processing device of the invention comprises an image signal input step, a color information acquisition step, and a saturation enhancement processing step. In the image signal input step, a color image signal is input to an image signal input unit. In the color information acquisition step, a color information acquisition unit acquires a plurality of pieces of color information from the color image signal. In the saturation enhancement processing step, a saturation enhancement processing unit executes saturation enhancement processing on a high saturation range on a high saturation side with respect to at least a specific saturation boundary line in a feature space formed from the plurality of pieces of color information to make differences in saturation among a plurality of observation target ranges distributed as an observation target large. In the saturation enhancement processing step, as the saturation enhancement processing, first saturation enhancement processing or second saturation enhancement processing different from the first saturation enhancement processing is executed. The high saturation range after the second saturation enhancement processing is greater than the high saturation range after the first saturation enhancement processing, and a value included in the high saturation range after the second saturation enhancement processing is smaller than a value included in the high saturation range after the first saturation enhancement processing.

According to the invention, in a case of executing processing for enhancing a difference in saturation between a normal part and an abnormal part, it is possible to extend a range of high saturation to increase visibility of an observation target while suppressing saturation enhancement of the observation target included in the range of high saturation.

BRIEF DESCRIPTION OF THE DRAWINGS

FIG. 15 is an explanatory view showing the distributions of the normal mucosa, the atrophic mucosa, the deep blood vessel, the BA, and reddening before and after saturation enhancement processing and hue enhancement processing in an ab space.

FIG. 17 is an explanatory view showing a setting menu screen.

DESCRIPTION OF THE PREFERRED EMBODIMENTS

First Embodiment

Figure 1:
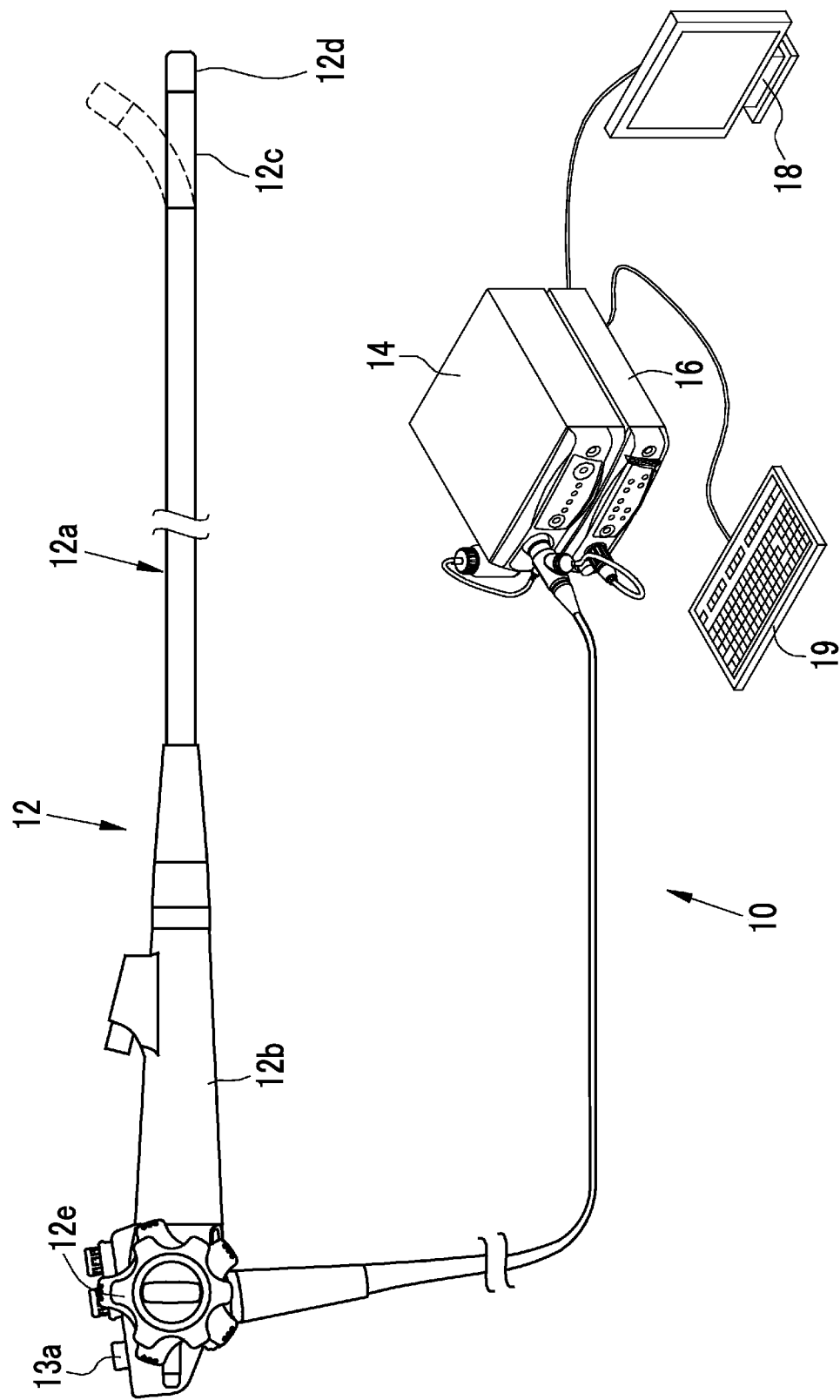
FIG. 1 is an appearance diagram of an endoscope system of a first embodiment.

As shown in FIG. 1, an endoscope system 10 of a first embodiment has an endoscope 12, a light source device 14, a processor device 16, a monitor 18, and a console (keyboard) 19. The endoscope 12 is optically connected to the light source device 14, and is electrically connected to the processor device 16. The endoscope 12 has an insertion portion 12a that is inserted into a subject, an operation portion 12b that is provided in a base portion of the insertion portion 12a, and a bending portion 12c and a tip portion 12d that are provided on the tip side of the insertion portion 12a. The bending portion 12c is bent by operating an angle knob 12e of the operation portion 12b. The tip portion 12d is directed in a desired direction with this bending operation.

The operation portion 12b is provided with a mode selection SW 13a, in addition to the angle knob 12e. The mode selection SW 13a is used for a switching operation between a normal observation mode and a special observation mode. The special observation mode is a mode in which a special image is displayed on the monitor 18. As a mode switching unit for switching between the modes, a foot switch may be used, in addition to the mode selection SW 13a.

The special image is one of three kinds of an inflammation evaluation image that is an image subjected to saturation enhancement and is suitable for inflammation evaluation of a colon, a UC screening image that is an image with more suppressed saturation enhancement than the inflammation evaluation image and is suitable for screening of ulcerative colitis (UC), and a normal image that is not subjected to special saturation enhancement unlike the inflammation evaluation image or the UC screening image. In a case where the special observation mode is set, an inflammation evaluation mode in which the inflammation evaluation image is displayed on the monitor 18 and a UC screening mode in which the UC screening image is displayed on the monitor 18 are automatically switched by a mode controller 85. In a case where the special observation mode is set, switching to a normal mode is performed by the operation on the mode selection SW 13a, whereby the normal image is displayed on the monitor 18.

The processor device 16 is electrically connected to the monitor 18 and the console 19. The monitor 18 outputs and displays image information or the like. The console 19 functions as a user interface (UI) that receives an input operation, such as function setting. An external recording unit (not shown) that records image information or the like may be connected to the processor device 16.

Figure 2:
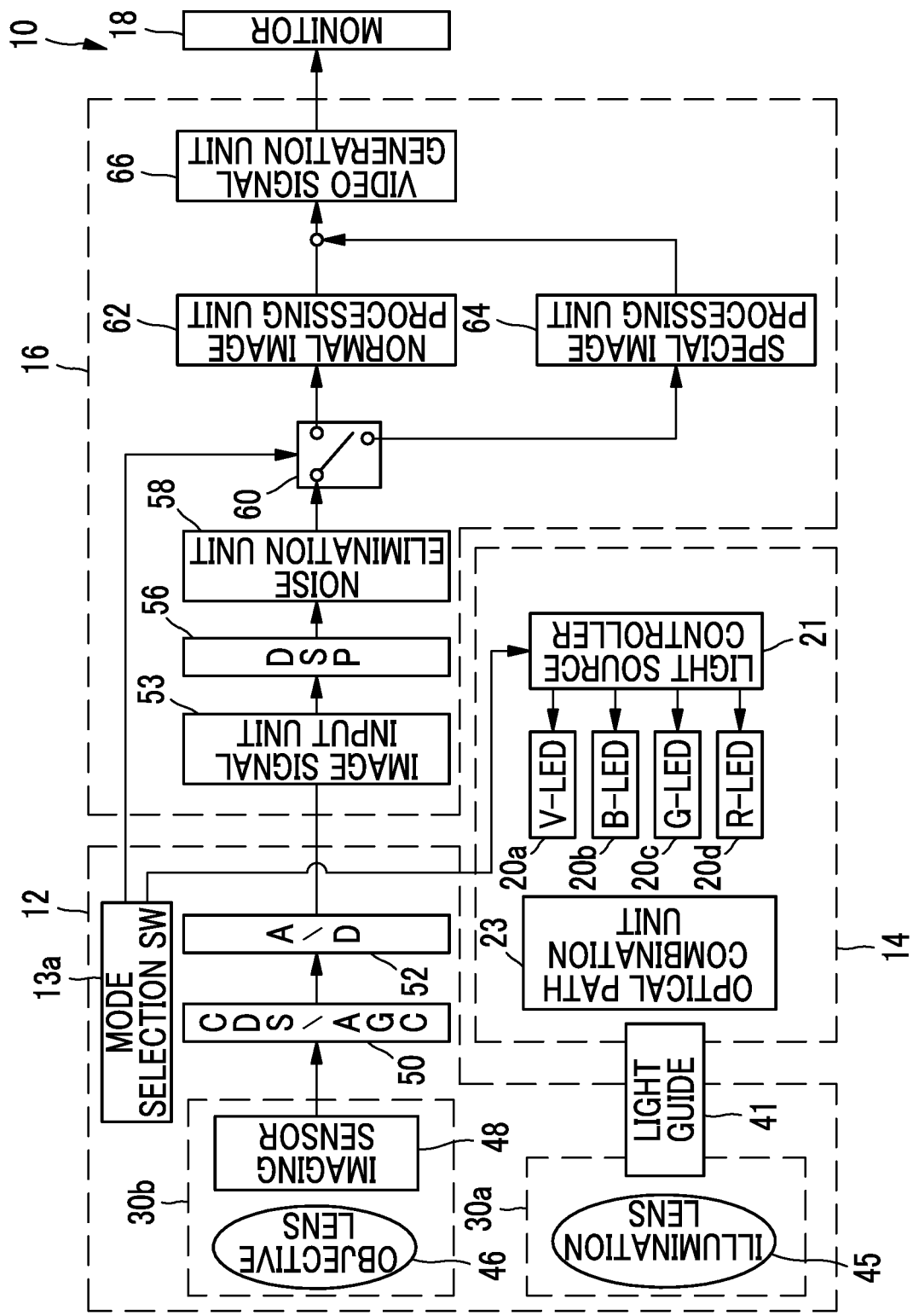
FIG. 2 is a block diagram showing functions of the endoscope system of the first embodiment.

As shown in FIG. 2, the light source device 14 comprises a violet light emitting diode (V-LED) 20a, a blue light emitting diode (B-LED) 20b, a green light emitting diode (G-LED) 20c, a red light emitting diode (R-LED) 20d, a light source controller 21 that controls driving of the LEDs 20a to 20d of the four colors, and an optical path combination unit 23 that combines the optical paths of light of four colors emitted from the LEDs 20a to 20d of the four colors. The inside of the subject is irradiated with light coupled by the optical path combination unit 23 through a light guide 41 and an illumination lens 45 inserted into the insertion portion 12a. A laser diode (LD) may be used instead of the LED.

Figure 3:
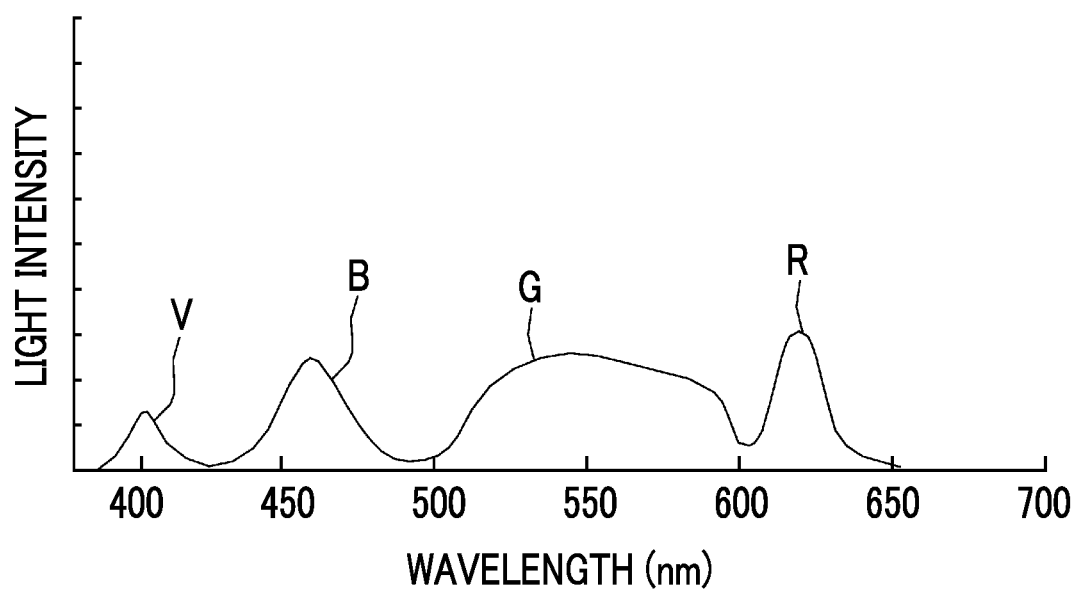
FIG. 3 is a graph showing light emission spectra of violet light V, blue light B, green light G, and red light R.

As shown in FIG. 3, the V-LED 20a generates violet light V having a center wavelength of 405±10 nm and a wavelength range of 380 nm to 420 nm. The B-LED 20b generates blue light B having a center wavelength of 460±10 nm and a wavelength range of 420 nm to 500 nm. The G-LED 20c generates green light G having a wavelength range of 480 nm to 600 nm. The R-LED 20d generates red light R having a center wavelength of 620 nm to 630 nm and a wavelength range of 600 nm to 650 nm.

The light source controller 21 turns on the V-LED 20a, the B-LED 20b, the G-LED 20c, and the R-LED 20d in any observation mode of the normal observation mode and the special observation mode. Accordingly, an observation target is irradiated with mixed light of light of the four colors of violet light V, blue light B, green light G, and red light R. In the normal observation mode, the light source controller 21 controls the LEDs 20a to 20d such that a light quantity ratio among violet light V, blue light B, green light G, and red light R becomes Vc:Bc:Gc:Rc. In the special observation mode, the light source controller 21 controls the LEDs 20a to 20d such that the light quantity ratio among violet light V, blue light B, green light G, and red light R becomes Vs:Bs:Gs:Rs.

As shown in FIG. 2, the light guide 41 is embedded in the endoscope 12 and a universal cord (a cord connecting the endoscope 12, the light source device 14, and the processor device 16), and light combined by the optical path combination unit 23 propagates to the tip portion 12d of the endoscope 12. As the light guide 41, a multi-mode fiber is available. As an example, a slender fiber cable that has a core diameter of 105 µm, a clad diameter of 125 µm, and a diameter φ of 0.3 to 0.5 mm including a protective layer as a sheath is available.

The tip portion 12d of the endoscope 12 is provided with an illumination optical system 30a and an imaging optical system 30b. The illumination optical system 30a has an illumination lens 45, and the observation target is irradiated with light from the light guide 41 through the illumination lens 45. The imaging optical system 30b has an objective lens 46 and an imaging sensor 48. Reflected light from the observation target is incident on the imaging sensor 48 through the objective lens 46. With this, a reflected image of the observation target is formed on the imaging sensor 48.

The imaging sensor 48 is a color imaging sensor, captures a reflected image of the subject, and output an image signal. It is preferable that the imaging sensor 48 is a charge coupled device (CCD) imaging sensor, a complementary metal-oxide semiconductor (CMOS) imaging sensor, or the like. The imaging sensor 48 used in the invention is a color imaging sensor for obtaining an RGB image signal of three colors of red (R), green (G), and blue (B), that is, a so-called RGB imaging sensor comprising R pixels with R filters, G pixels with G filters, and B pixels with B filters.

The imaging sensor 48 may be a so-called complementary color imaging sensor comprising complementary color filters of cyan (C), magenta (M), yellow (Y), and green (G), instead of the RGB color imaging sensor. In a case where the complementary color imaging sensor is used, since image signals of four colors of CMYG are output, it is necessary to convert the image signals of the four colors of CMYG to image signals of three colors of RGB through complementary color/primary color conversion. The imaging sensor 48 may be a monochrome imaging sensor with no color filters. In this case, it is necessary that the light source controller 21 turns on blue light B, green light G, and red light R in a time-division manner, and it is necessary also to synchronize processing of captured signals.

The image signals output from the imaging sensor 48 are transmitted to a CDS/AGC circuit 50. The CDS/AGC circuit 50 performs correlated double sampling (CDS) or automatic gain control (AGC) on the image signals as analog signals. The image signals having passed through the CDS/AGC circuit 50 are converted to digital image signals by an analog/digital (A/D) converter 52. The A/D-converted digital image signals are input to the processor device 16.

The processor device 16 corresponds to a medical image processing device that processes a medical image, such as an image obtained by the endoscope 12. The processor device 16 comprises an image signal input unit 53, a digital signal processor (DSP) 56, a noise elimination unit 58, a signal switching unit 60, a normal image processing unit 62, a special image processing unit 64, and a video signal generation unit 66. To the image signal input unit 53, a digital color image signal from the endoscope 12 is input. The color image signal is an RGB image signal constituted of an R image signal output from the R pixel of the imaging sensor 48, a G image signal output from the G pixel of the imaging sensor 48, and a B image signal output from the B pixel of the imaging sensor 48.

The DSP 56 subjects the received image signals to various kinds of signal processing, such as defect correction processing, offset processing, gain correction processing, linear matrix processing, gamma conversion processing, or demosaic processing. In the defect correction processing, signals from defective pixels of the imaging sensor 48 are corrected. In the offset processing, dark current components are removed from the RGB image signal subjected to the defect correction processing, and an accurate zero level is set. In the gain correction processing, a signal level is adjusted by multiplying the RGB image signal after the offset processing by a specific gain. The RGB image signal after the gain correction processing is subjected to the linear matrix processing for increasing color reproducibility. Thereafter, brightness or saturation is adjusted by the gamma conversion processing. The RGB image signal after the linear matrix processing is subjected to the demosaic processing (also referred to as equalization processing or synchronization processing), and signals of colors lacking in each pixel are generated by interpolation. With the demosaic processing, all pixels have signals of the respective colors of RGB.

The noise elimination unit 58 executes noise elimination processing (for example, a moving average method, a median filter method, or the like) on the RGB image signals subjected to gamma correction or the like in the DSP 56 to eliminate noise from the RGB image signals. The noise-eliminated RGB image signals are transmitted to the signal switching unit 60.

The signal switching unit 60 transmits the RGB image signals to the normal image processing unit 62 in a case where the normal observation mode is set by the mode selection SW 13a, and transmits the RGB image signals to the special image processing unit 64 in a case where the special observation mode is set.

The normal image processing unit 62 executes image processing for a normal image on the RGB image signal. In the image processing for a normal image, structure enhancement processing for a normal image and the like are included. The RGB image signal subjected to the image processing for a normal image is input as the normal image from the normal image processing unit 62 to the video signal generation unit 66.

Based on the image signals of RGB, the special image processing unit 64 generates, as the special image, the inflammation evaluation image that is an image subjected to saturation enhancement and is suitable for inflammation evaluation of a colon, the UC screening image that is an image with more suppressed saturation enhancement than the inflammation evaluation image and is suitable for screening of ulcerative colitis, and the normal image that is not subjected to special saturation enhancement unlike the inflammation evaluation image or the UC screening image. Details of the special image processing unit 64 will be described below. The special image generated by the special image processing unit 64 is input to the video signal generation unit 66.

The video signal generation unit 66 converts the normal image or the special image input from the normal image processing unit 62 or the special image processing unit 64 to a video signal for display as an image displayable on the monitor 18. The monitor 18 displays the normal image or the special image based on the video signal.

Figure 4:
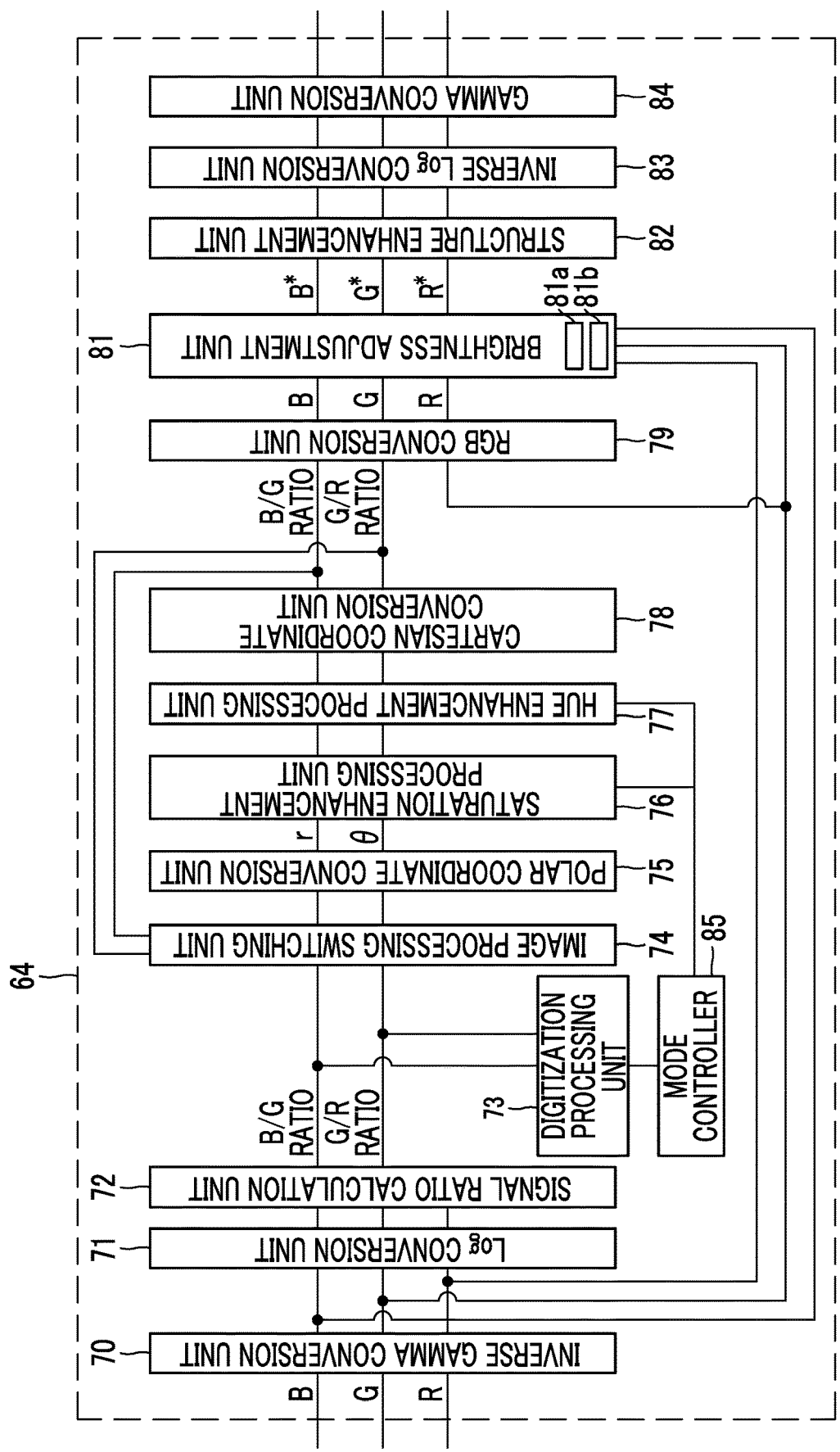
FIG. 4 is a block diagram showing functions of a first special image processing unit for use in a case where a feature space is a signal ratio space.

As shown in FIG. 4, the special image processing unit 64 comprises an inverse gamma conversion unit 70, a Log conversion unit 71, a signal ratio calculation unit 72, a digitization processing unit 73, an image processing switching unit 74, a polar coordinate conversion unit 75, a saturation enhancement processing unit 76, a hue enhancement processing unit 77, a Cartesian coordinate conversion unit 78, an RGB conversion unit 79, a brightness adjustment unit 81, a structure enhancement unit 82, an inverse Log conversion unit 83, and a gamma conversion unit 84. The special image processing unit 64 is provided with the mode controller 85 that controls the image processing switching unit 74, and controls the saturation enhancement processing unit 76 and the hue enhancement processing unit 77.

In the special image processing unit 64, in a case where the inflammation evaluation mode (first mode) is set, first saturation enhancement processing is executed by the saturation enhancement processing unit 76, and first hue enhancement processing is executed by the hue enhancement processing unit 77, whereby the inflammation evaluation image (first saturation enhanced image) is generated. In a case where the UC screening mode (second mode) is set, second saturation enhancement processing is executed by the saturation enhancement processing unit 76, and second hue enhancement processing is executed by the hue enhancement processing unit 77, whereby the UC screening image (second saturation enhanced image) is generated. In a case where the normal mode (third mode) is set, the normal image is generated without executing saturation enhancement processing by the saturation enhancement processing unit 76 and without executing hue enhancement processing by the hue enhancement processing unit 77.

The inverse gamma conversion unit 70 subjects the input digital image signal of three RGB channels to inverse gamma conversion. Since the RGB image signals after inverse gamma conversion are reflectance linear RGB signals that are linear with respect to reflectance from the subject, the ratio of a signal associated with various kinds of biological information of the subject among the RGB image signals becomes high. The reflectance linear R image signal is referred to as a first R image signal, the reflectance linear G image signal is referred to as a first G image signal, and the reflectance linear B image signal is referred to as a first B image signal. The first R image signal, the first G image signal, and the first B image signal are collectively referred to as a first RGB image signal.

The Log conversion unit 71 subjects the reflectance linear RGB image signal to Log conversion. With this, an R image signal (log R) subjected to Log conversion, a G image signal (log G) subjected to Log conversion, and a B image signal (log B) subjected to Log conversion are obtained. The signal ratio calculation unit 72 (corresponding to a "color information acquisition unit" of the invention) executes differential processing (log G–log B=log G/B=–log(B/G)) based on the G image signal and the B image signal subjected to Log conversion to calculate the B/G ratio (the "B/G ratio" refers to –log(B/G) with "–log" omitted). Differential processing (log R–log G=log R/G=–log(G/R)) is executed based on the R image signal and the G image signal subjected to Log conversion to calculate the G/R ratio. Similarly to the B/G ratio, the G/R ratio refers to –log(G/R) with "–log" omitted.

The B/G ratio and the G/R ratio are obtained from the pixel values of the pixels at the same positions in the B image signal, the G image signal, and the R image signal for each pixel. The B/G ratio and the G/R ratio are obtained for each pixel. The B/G ratio correlates with a blood vessel depth (the distance between the mucosal surface and a position of a specific blood vessel); thus, the B/G ratio varies with a difference in blood vessel depth. The G/R ratio correlates with a blood volume (hemoglobin index); thus, the G/R ratio varies with variation in blood volume.

The digitization processing unit 73 executes digitization processing for digitizing an inflammation state of the observation target, such as a colon, based on the B/G ratio and the G/R ratio obtained by the signal ratio calculation unit 72. A value obtained through the digitization processing is sent to the mode controller 85. The mode controller 85 controls the image processing switching unit 74, the saturation enhancement processing unit 76, and the hue enhancement processing unit 77 based on the value obtained through the digitization processing. Details of the digitization processing unit 73 and the mode controller 85 will be described below.

The polar coordinate conversion unit 75 converts the B/G ratio and the G/R ratio obtained by the signal ratio calculation unit 72 to a radius vector r and an angle θ. The polar coordinate conversion unit 75 performs the conversion to the radius vector r and the angle θ for all pixels. The saturation enhancement processing unit 76 expands or compresses the radius vector r, thereby executing the saturation enhancement processing for making the difference in saturation between an observation target range included in the observation target large. In the saturation enhancement processing that is executed by the saturation enhancement processing unit 76, the first saturation enhancement processing that is executed in a case where the inflammation evaluation mode is set and the second saturation enhancement processing that is executed in a case where the UC screening mode is set are included. The second saturation enhancement processing has the degree of enhancement of saturation lower than the first saturation enhancement processing. Details of the saturation enhancement processing unit 76 will be described below.

The hue enhancement processing unit 77 expands or compresses the angle θ, thereby executing the hue enhancement processing for making the differences in hue among a plurality of observation target ranges large. In the hue enhancement processing that is executed by the hue enhancement processing unit 77, the first hue enhancement processing that is executed in a case where the inflammation evaluation mode is set and the second hue enhancement processing that is executed in a case where the UC screening mode is set are included. The second hue enhancement processing has the degree of enhancement of hue higher than the first hue enhancement processing. Details of the hue enhancement processing unit 77 will be described below.

The Cartesian coordinate conversion unit 78 converts the radius vector r and angle θ subjected to the saturation enhancement processing and the hue enhancement processing to Cartesian coordinates. With this, the radius vector r and angle θ are converted to the B/G ratio and the G/R ratio subjected to angle expansion and compression. The RGB conversion unit 79 converts the B/G ratio and the G/R ratio subjected to the saturation enhancement processing and the hue enhancement processing to a second RGB image signal using at least one image signal in the first RGB image signal. For example, the RGB conversion unit 79 converts the B/G ratio to the second B image signal by performing arithmetic operation based on the first G image signal in the first RGB image signal and the B/G ratio. The RGB conversion unit 79 converts the G/R ratio to the second R image signal by performing arithmetic operation based on the first G image signal in the first RGB image signal and the G/R ratio. The RGB conversion unit 79 outputs the first G image signal as the second G image signal without performing special conversion. The second R image signal, the second G image signal, and the second B image signal are collectively referred to as a second RGB image signal.

The brightness adjustment unit 81 adjusts the pixel values of the second RGB image signal using the first RGB image signal and the second RGB image signal. The reason that the brightness adjustment unit 81 adjusts the pixel values of the second RGB image signal is as follows. The second RGB image signals obtained by expanding or compressing the color areas in the saturation enhancement processing unit 76 and the hue enhancement processing unit 77 may be significantly changed in brightness from the first RGB image signal. Accordingly, the brightness adjustment unit 81 adjusts the pixel values of the second RGB image signal to make the second RGB image signal after brightness adjustment equal in brightness to the first RGB image signal.

The brightness adjustment unit 81 comprises a first brightness information calculation unit 81a that obtains first brightness information Yin based on the first RGB image signal, and a second brightness information calculation unit 81b that obtains second brightness information Yout based on the second RGB image signal. The first brightness information calculation unit 81a calculates the first brightness information Yin according to an arithmetic expression "kr×pixel value of first R image signal+kg×pixel value of first G image signal+kb×pixel value of first B image signal". Similarly to the first brightness information calculation unit 81a, the second brightness information calculation unit 81b calculates the second brightness information Yout according to the same arithmetic expression as described above. In a case where the first brightness information Yin and the second brightness information Yout are obtained, the brightness adjustment unit 81 adjusts the pixel values of the second RGB image signal by performing arithmetic operation based on Expressions (E1) to (E3) described below.

$$R^* = \text{pixel value of second } R \text{ image signal} \times Yin/Yout \quad (E1)$$

$$G^* = \text{pixel value of second } G \text{ image signal} \times Yin/Yout \quad (E2)$$

$$B^* = \text{pixel value of second } B \text{ image signal} \times Yin/Yout \quad (E3)$$

"R*" represents the second R image signal after brightness adjustment, "G*" represents the second G image signal after brightness adjustment, and "B*" represents the second B image signal after brightness adjustment. "kr", "kg", and "kb" are arbitrary constants within a range of "0" to "1".

The structure enhancement unit 82 subjects the second RGB image signal having passed through the RGB conversion unit 79 to the structure enhancement processing. As the structure enhancement processing, frequency filtering or the like is used. The inverse Log conversion unit 83 subjects the second RGB image signals having passed through the structure enhancement unit 82 to inverse Log conversion. With this, the second RGB image signal having antilogarithmic pixel values is obtained. The gamma conversion unit 84 subjects the RGB image signal having passed through the inverse Log conversion unit 83 to gamma conversion. With this, the second RGB image signal having the gradation suitable for an output device, such as the monitor 18, is obtained. The second RGB image signal having passed through the gamma conversion unit 84 is sent to the video signal generation unit 66.

Figure 5:
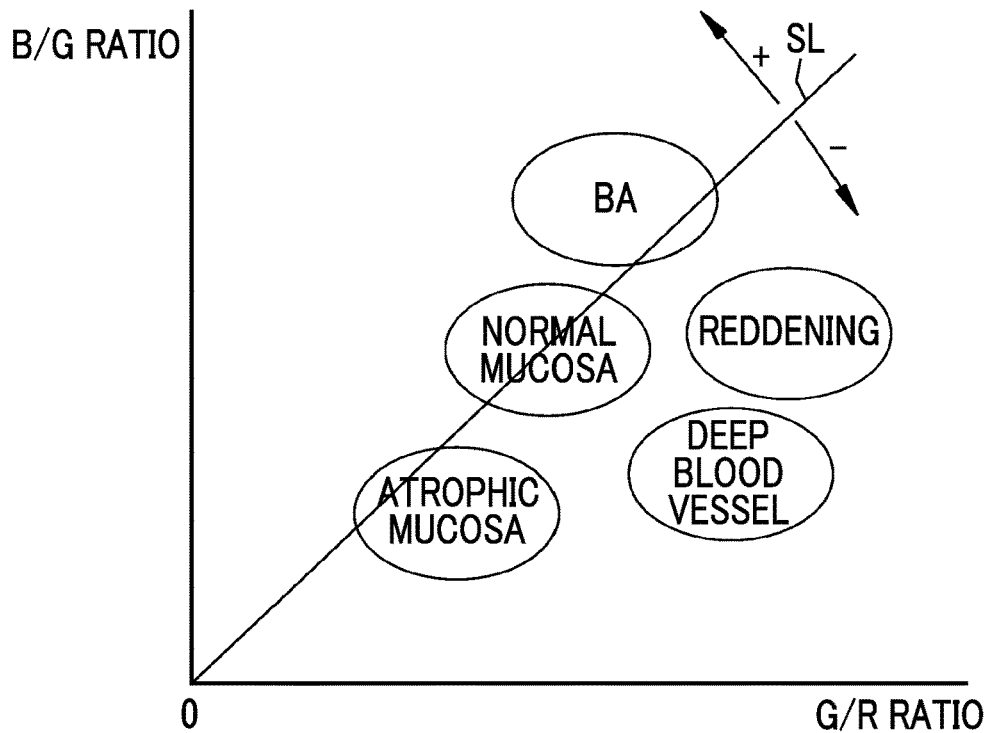
FIG. 5 is an explanatory view showing the ranges of a normal mucosa, an atrophic mucosa, a deep blood vessel, a BA, and reddening that are distributed in a signal ratio space.

In the saturation enhancement processing unit 76 and the hue enhancement processing unit 77, as shown in FIG. 5, the differences in saturation or the differences in hue among a first range including a normal mucosa, a second range including an atrophic mucosa, a third range including a deep blood vessel (hereinafter, simply referred to as a deep blood vessel) under the atrophic mucosa, a fourth range including a brownish area (BA), and a fifth range including reddening as a plurality of observation target ranges included in the observation target is made large. In a first quadrant of a signal ratio space (feature space) formed from the B/G ratio and the G/R ratio, the first range of the normal mucosa is substantially distributed at the center. The second range of the atrophic mucosa is positioned slightly in a clockwise direction (in a minus direction described below) with respect to a reference line SL passing through the first range of the normal mucosa, and is distributed at a position closer to the origin than the first range of the normal mucosa. The third range of the deep blood vessel is distributed in the clockwise direction (in the minus direction described below) with respect to the reference line SL. The fourth range of the BA is distributed slightly in a counterclockwise direction (in a plus direction described below) with respect to the reference line SL. The fifth range of reddening is distributed in the clockwise direction (in the minus direction described below) with respect to the reference line SL. The fourth range of the BA and the fifth range of reddening are distributed at positions farther from the origin than the first range of the normal mucosa. It is preferable that the normal mucosa is included in a normal part of the observation target, and the atrophic mucosa, the deep blood vessel, the BA, and reddening are included in an abnormal part of the observation target. The reference line SL corresponds to a hue reference line SLh described below.

The digitization processing unit 73 calculates observation target information obtained by digitizing the state of the observation target based on the B/G ratio and the G/R ratio obtained by the signal ratio calculation unit 72. Specifically, the degree of inflammation obtained by digitizing the inflamed state of the observation target is calculated as the observation target information. The calculated degree of inflammation is sent to the mode controller 85. In a case where a specific condition relating to the degree of inflammation is satisfied, for example, in a case where the degree of inflammation falls below a threshold, or the like, the mode controller 85 automatically performs switching to the inflammation evaluation mode. In a case where switching of the inflammation evaluation mode is performed, the mode controller 85 performs control such that the image processing switching unit 74 sends the B/G ratio and the G/R ratio to the saturation enhancement processing unit 76 and the hue enhancement processing unit 77.

In a case where a specific condition relating to the degree of inflammation is not satisfied, for example, in a case where the degree of inflammation exceeds the threshold, or the like, the mode controller 85 automatically performs switching to the UC screening mode. Even in a case where switching to the UC screening mode is performed, the mode controller 85 performs control such that the image processing switching unit 74 sends the B/G ratio and the G/R ratio to the saturation enhancement processing unit 76 and the hue enhancement processing unit 77. In a case where the normal mode is set, the mode controller 85 performs control such that the image processing switching unit 74 sends the B/G ratio and the G/R ratio to the RGB conversion unit 79 without passing through the saturation enhancement processing unit 76 and the hue enhancement processing unit 77.

As the degree of inflammation that is calculated by the digitization processing unit 73, it is preferable that an area ratio of pixels included in an inflamed area among all pixels of one screen is calculated. It is preferable that the inflamed area includes the fifth range of reddening. It is preferable that the area ratio is calculated by counting the pixels included in the inflamed area and dividing the total number of pixels of the inflamed area by the number of all pixels of one screen. The pixels in one screen refer to all pixels in an RGB image signal of one frame.

As the degree of inflammation, other than the area ratio, a value obtained by averaging numerical information obtained from one screen may be used. For example, values of a B/G ratio on a vertical axis or a G/R ratio on a horizontal axis corresponding to pixels distributed in a signal ratio space are given as the numerical information obtained from one screen, and an average value of the values of the B/G ratio on the vertical axis or the G/R ratio on the horizontal axis may be set as the degree of inflammation. In this case, the closer the average value of the values of the B/G ratio on the vertical axis or the G/R ratio on the horizontal axis to a representative value indicating an inflamed area determined in advance, the higher the degree of inflammation. As described below, in a case of an ab space, an average value of values of a* on a horizontal axis or b* on a vertical axis may be set as the degree of inflammation. In a case of a CrCb space, an average value of values of Cr on a horizontal axis or Cb on a vertical axis may be set as the degree of inflammation. In a case of an HS space, an average value of values of H on a horizontal axis or S on a vertical axis may be set as the degree of inflammation.

Figure 6:
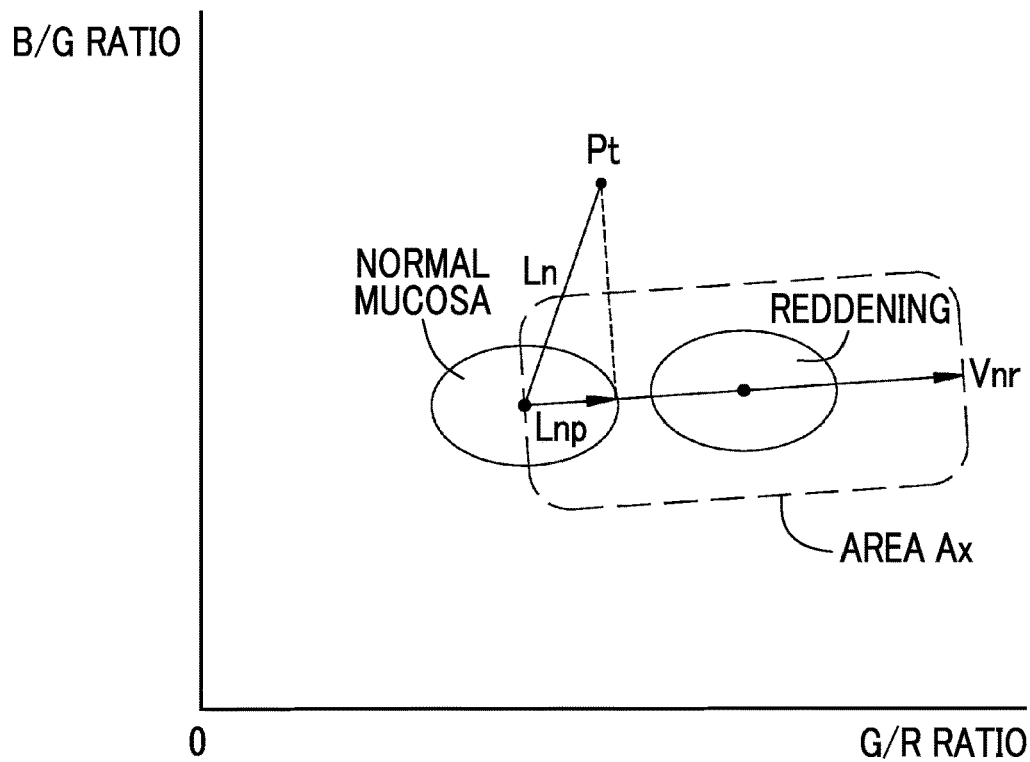
FIG. 6 is an explanatory view showing a distance Ln, a distance Lnp, a vector Vnr, and an area Ax.

In a case where the feature space is a signal ratio space, an ab space, and a CrCb space, angles θ corresponding to pixels distributed in the feature space are given as the numerical information obtained from one screen, and it is preferable that an average value of the angles θ is set as the degree of inflammation. In this case, the closer the average value of the angles θ to a representative value indicating an inflamed area determined in advance, the higher the degree of inflammation. In the feature space, the distance to the first range of the normal mucosa or the distance to the fifth range of reddening is given as the numerical information obtained from one screen, and it is preferable that an average value of the distances is set as the degree of inflammation. The greater the distance to the first range of the normal mucosa, the greater the degree of inflammation. The smaller the distance from the fifth range of reddening, the smaller the degree of inflammation. As shown in FIG. 6, the distance from the first range of the normal mucosa is represented by the distance Ln between a specific pixel Pt and a predetermined pixel included in the first range of the normal mucosa.

The distance to the first range of the normal mucosa is set to a distance in a case where a pixel is projected on a vector Vnr connecting the first range of the normal mucosa and the fifth range of reddening in the feature space. For example, in a case where the specific pixel Pt is projected on the vector Vnr, the distance to the first range of the normal mucosa becomes Lnp.

Instead of using the value obtained by averaging the numerical information obtained from one screen as the degree of inflammation, a median value of a histogram based on the numerical information obtained from one screen may be set as the degree of inflammation. Alternatively, a value obtained by averaging numerical information included in a specific pixel area of 100 pixels×100 pixels at the center of the screen in one screen may be used as the degree of inflammation. In a case of measuring the degree of inflammation of a specific position, it is preferable that position designation means shown in FIG. 6 or the like of JP2009-226095A is used. In JP2009-226095A, a plurality of rectangular areas (for example, nine rectangular areas) are displayed in a superimposed manner on the screen, and a portion to be measured where the degree of inflammation is desired to be measured enters the central rectangular area among the rectangular areas. Then, when the portion to be measured enters the central rectangular area, the console 19 or the like is operated to measure the degree of inflammation of the portion to be measured. In a case where a value obtained by averaging numerical information obtained from one screen is used as the degree of inflammation, average processing may be executed excluding numerical information of pixels included in the area Ax (see FIG. 6). With the execution of such average processing, since it is possible to exclude, for example, a residue or a point unneeded for calculating the degree of inflammation, such as a deep blood vessel, it is possible to accurately calculate the degree of inflammation of a mucosa.

Figure 7:
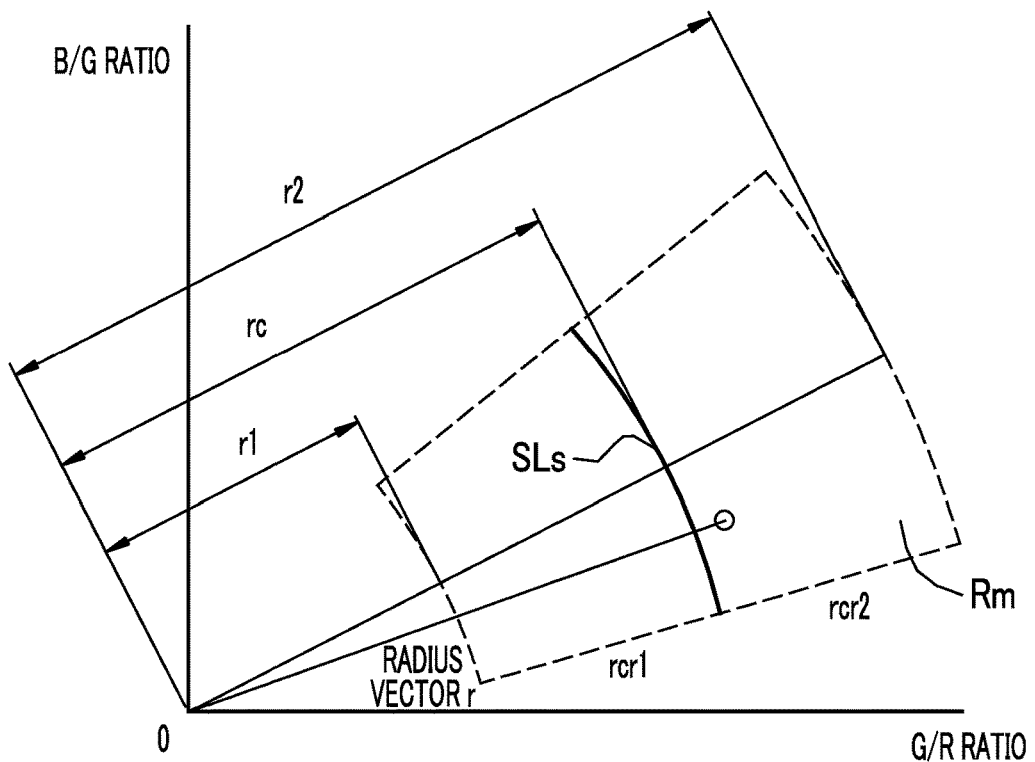
FIG. 7 is an explanatory view showing a radius vector change range Rm.

As shown in FIG. 7, in the saturation enhancement processing unit 76, while the radius vector r indicated by coordinates within a radius vector change range Rm in the signal ratio space is changed, the radius vector r is not changed for coordinates outside a radius vector change range Rx. In the radius vector change range Rm, the radius vector r is within a range of "r1" to "r2" (r1<r2). In the radius vector change range Rm, a saturation reference line SLs is set on a radius vector rc between the radius vector r1 and the radius vector r2. Here, since the greater the radius vector r, the higher the saturation, a range rcr1 (r1<r<rc) in which the radius vector r is smaller than the radius vector rc indicated by the saturation reference line SLs is considered to be a low saturation range. A range rcr2 (rc<r<r2) in which the radius vector r is greater than the radius vector rc indicated by the saturation reference line SLs is considered to be a high saturation range.

Figure 8:
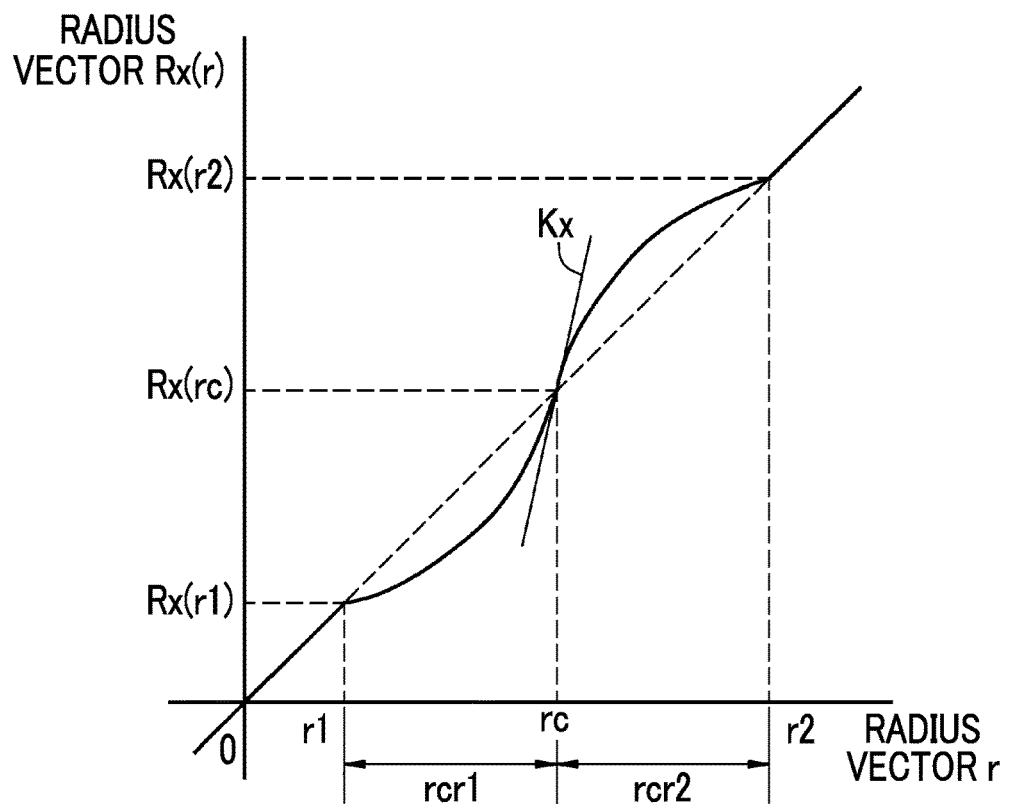
FIG. 8 is a graph showing the relationship between a radius vector r and a radius vector Rx(r) after first saturation enhancement processing.

In the saturation enhancement processing unit 76, in a case where the inflammation evaluation mode is set, the first saturation enhancement processing is executed. As shown in FIG. 8, the first saturation enhancement processing outputs a radius vector Rx(r) to an input of the radius vector r of the coordinates included within the radius vector change range Rm. The input-output relationship in the first saturation enhancement processing is represented by a solid line. In the first saturation enhancement processing, while the output Rx(r) is made smaller than the input r in the low saturation range rcr1, the output Rx(r) is made greater than the input r in the high saturation range rcr2. An inclination Kx at Rx(rc) is set to be equal to or greater than "1". With this, while the saturation of an observation target included in the low saturation range can be made lower, the saturation of an observation target included in the high saturation range can be made higher. With such saturation enhancement, it is possible to increase the differences in saturation among a plurality of observation target ranges.

Figure 9:
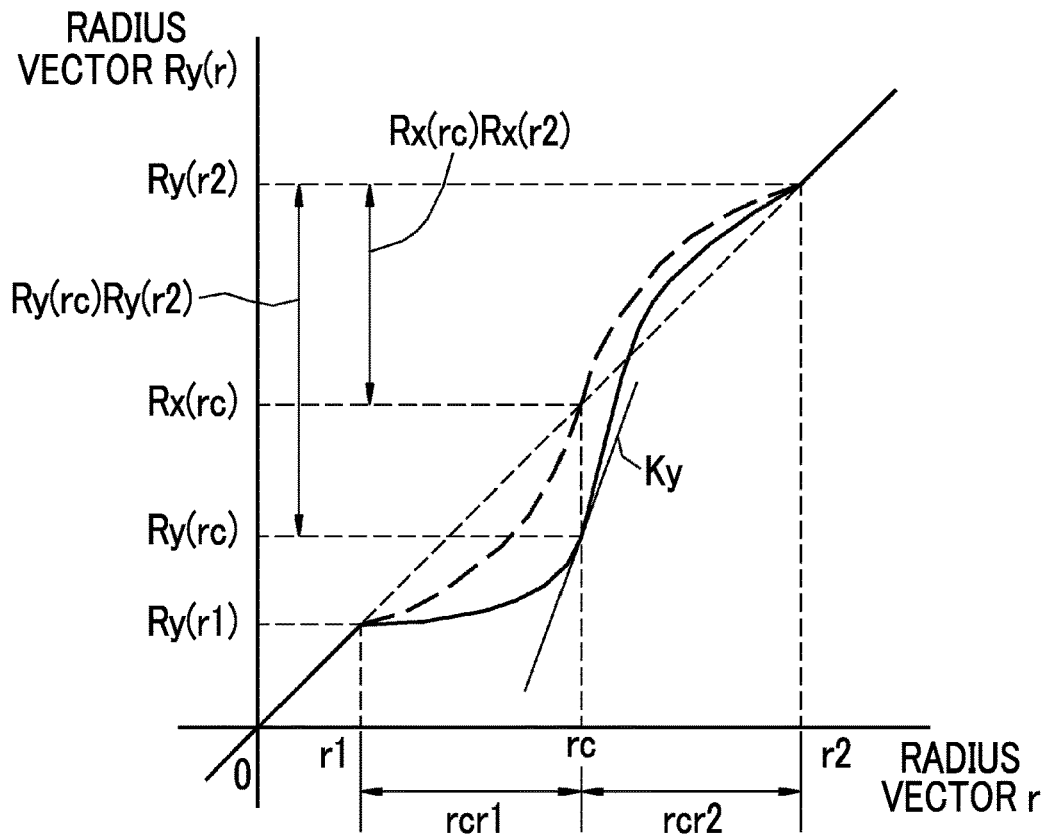
FIG. 9 is a graph showing the relationship between the radius vector r and a radius vector Ry(r) after second saturation enhancement processing.

In the saturation enhancement processing unit 76, in a case where the UC screening mode is set, the second saturation enhancement processing is executed. As shown in FIG. 9, the second saturation enhancement processing outputs a radius vector Ry(r) to an input of the radius vector r of the coordinates included within the radius vector change range Rm. The input-output relationship in the second saturation enhancement processing is represented by a solid line. In the second saturation enhancement processing, the output Ry(r) is made smaller than the input r in the low saturation range rcr1. In contrast, in the high saturation range rcr2, while the output Ry(r) is made smaller than the input r on a low saturation side close to the radius vector rc, the output Rx(r) is made greater than the input r on a high saturation side distant from the radius vector rc. An inclination Ky at Ry(rc) is set to be equal to or greater than "1".

With this, while the saturation of an observation target included on the low saturation side of the low saturation range rcr1 and the high saturation range rcr2 can be made lower, the saturation of an observation target included on the high saturation side of the high saturation range rcr2 can be made higher. With such saturation enhancement, it is possible to increase the difference in saturation between the observation target on the low saturation side of the low saturation range rcr1 or the high saturation range rcr2 and the observation target on the high saturation side of the high saturation range rcr2.

It should be noted that, in order to improve the visibility of the deep blood vessel, the second saturation enhancement processing suppresses the saturation enhancement in the high saturation range rcr2 compared to the first saturation enhancement processing. For this reason, the high saturation range Ry(rc)Ry(r2) after the second saturation enhancement processing is made greater than the high saturation range Rx(rc)Rx(r2) after the first saturation enhancement processing. Here, the input-output relationship in the first saturation enhancement processing is represented by a dotted line. In addition, the value Ry(r) included in the high saturation range Ry(rc)Ry(r2) after the second saturation enhancement processing is made smaller than the value Rx(r) included in the high saturation range Rx(rc)Rx(r2) after the first saturation enhancement processing. With this, since the saturation enhancement in the high saturation range rcr2 is suppressed, and the visibility of the deep blood vessel is improved, it is possible to improve diagnosis accuracy of a colon, such as ulcerative colitis.

Figure 10:
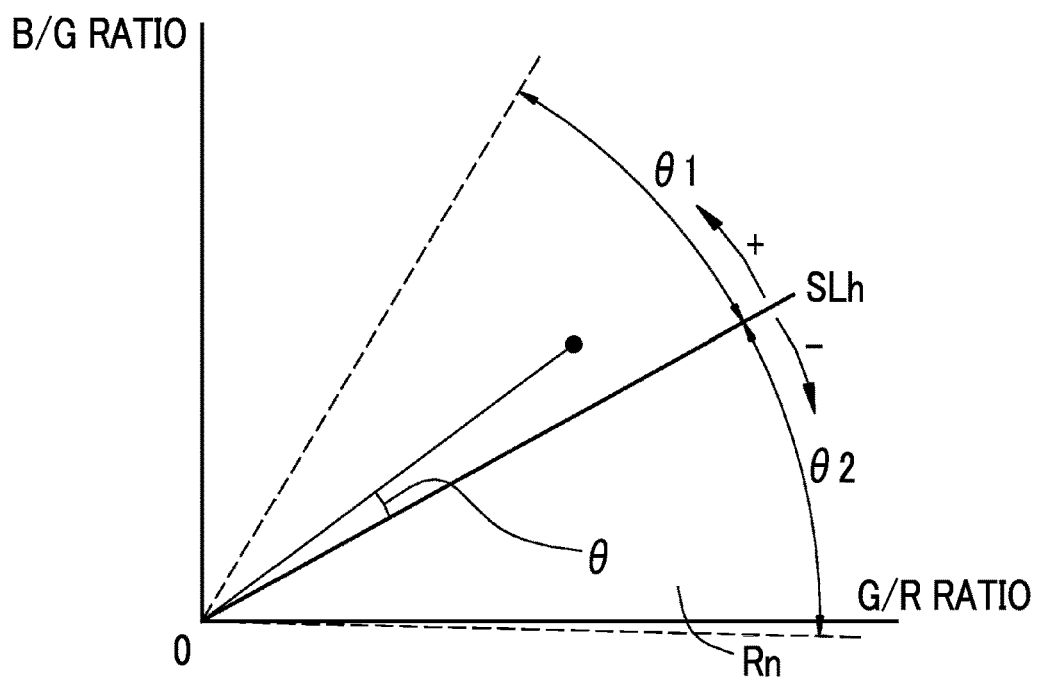
FIG. 10 is an explanatory view showing an angle change range Rn.

As shown in FIG. 10, in the hue enhancement processing unit 77, while an angle θ indicated by coordinates within an angle change range Rn in the signal ratio space is changed, the angle θ is not changed for coordinates outside the angle change range Rn. The angle change range Rn is constituted of a range of an angle θ1 in a counterclockwise direction (plus direction) from the hue reference line SLh and a range of an angle θ2 in a clockwise direction (minus direction) from the hue reference line SLh. The angle θ of the coordinates included in the angle change range Rn is re-defined by the angle θ with respect to the hue reference line SLh. In a case where the angle θ changes, the hue also changes. Accordingly, in the angle change range Rn, the range of the angle θ1 is set as a plus-side hue range θ1, and the range of the angle θ2 is set as a minus-side hue range θ2.

Figure 11:
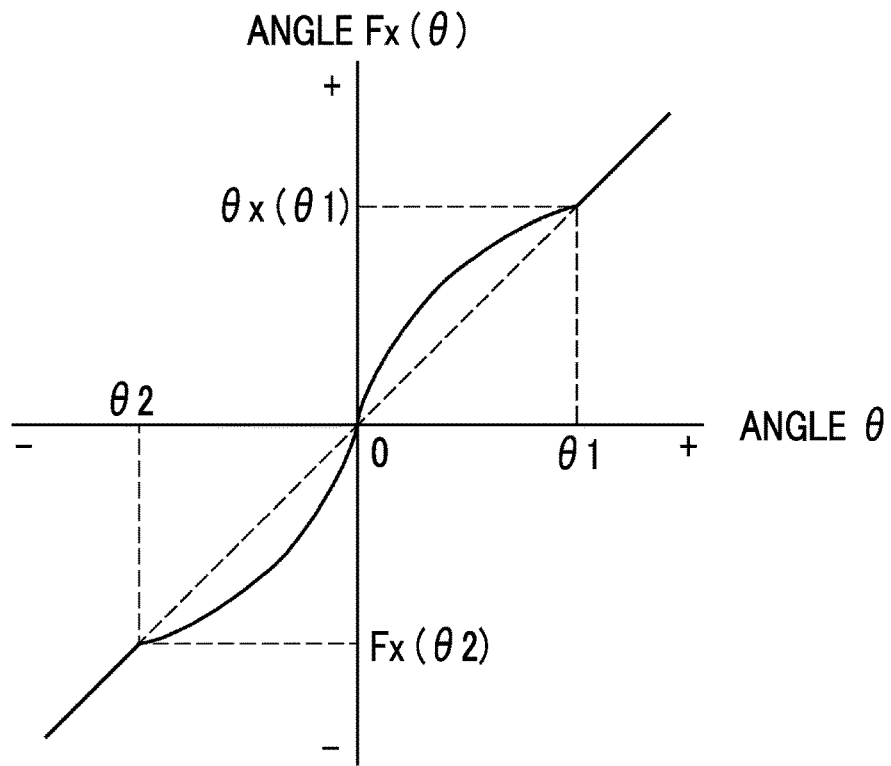
FIG. 11 is a graph showing the relationship between an angle $\theta$ and an angle Fx($\theta$) after first hue enhancement processing.

In the hue enhancement processing unit 77, in a case where the inflammation evaluation mode is set, the first hue enhancement processing is executed. As shown in FIG. 11, the first hue enhancement processing outputs an angle Fx(θ) to an input of the angle θ of the coordinates included within the angle change range Rn. The input-output relationship in the first hue enhancement processing is represented by a solid line. In the first hue enhancement processing, while the output Fx(θ) is made smaller than the input θ in the minus-side hue range θ2, the output Fx(θ) is made greater than the input θ in the plus-side hue range θ1. With this, it is possible to increase the difference in hue between an observation target included in the minus-side hue range and an observation target included in the plus-side hue range. With such hue enhancement, it is possible to increase the differences in hue among a plurality of observation target ranges.

Figure 12:
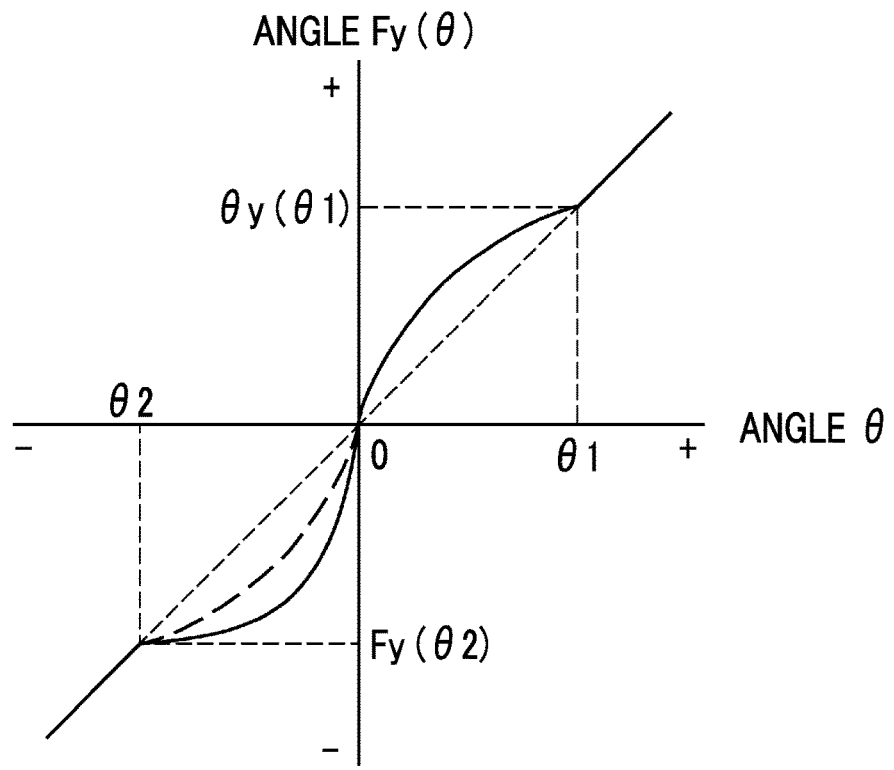
FIG. 12 is a graph showing the relationship between the angle $\theta$ and an angle Fy($\theta$) after second hue enhancement processing.

In the hue enhancement processing unit 77, in a case where the UC screening mode is set, the second hue enhancement processing is executed. As shown in FIG. 12, the second hue enhancement processing outputs an angle Fy(θ) to an input of the angle θ of the coordinates included within the angle change range Rn. The input-output relationship in the second hue enhancement processing is represented by a solid line. In the second hue enhancement processing, while the output Fx(θ) is made smaller than the input θ in the minus-side hue range θ2, the output Fx(θ) is made greater than the input θ in the plus-side hue range θ1. With this, it is possible to increase the difference in hue between an observation target included in the minus-side hue range and an observation target included in the plus-side hue range. With such hue enhancement, it is possible to increase the differences in hue among a plurality of observation target ranges.

It should be noted that, in the second hue enhancement processing, in order to improve the visibility of the deep blood vessel, the hue enhancement of the hue range θ2 (specific hue range) on the minus side (in a specific hue direction) included in the third range of the deep blood vessel is made more intense than in the first hue enhancement processing. For this reason, the angle θ included in the minus-side hue range Fy(θ) after the second hue enhancement processing is made smaller than the angle θ included in the minus-side hue range Fx(θ) after the first hue enhancement processing. Here, the input-output relationship in the first hue enhancement processing is represented by a dotted line. In this way, the hue enhancement in the minus-side hue range θ is intensified, it is possible to increase the difference in hue between the third range of the deep blood vessel and other observation target ranges. With this, since the visibility of the deep blood vessel is improved, it is possible to improve diagnosis accuracy of a colon, such as ulcerative colitis.

Figure 13:
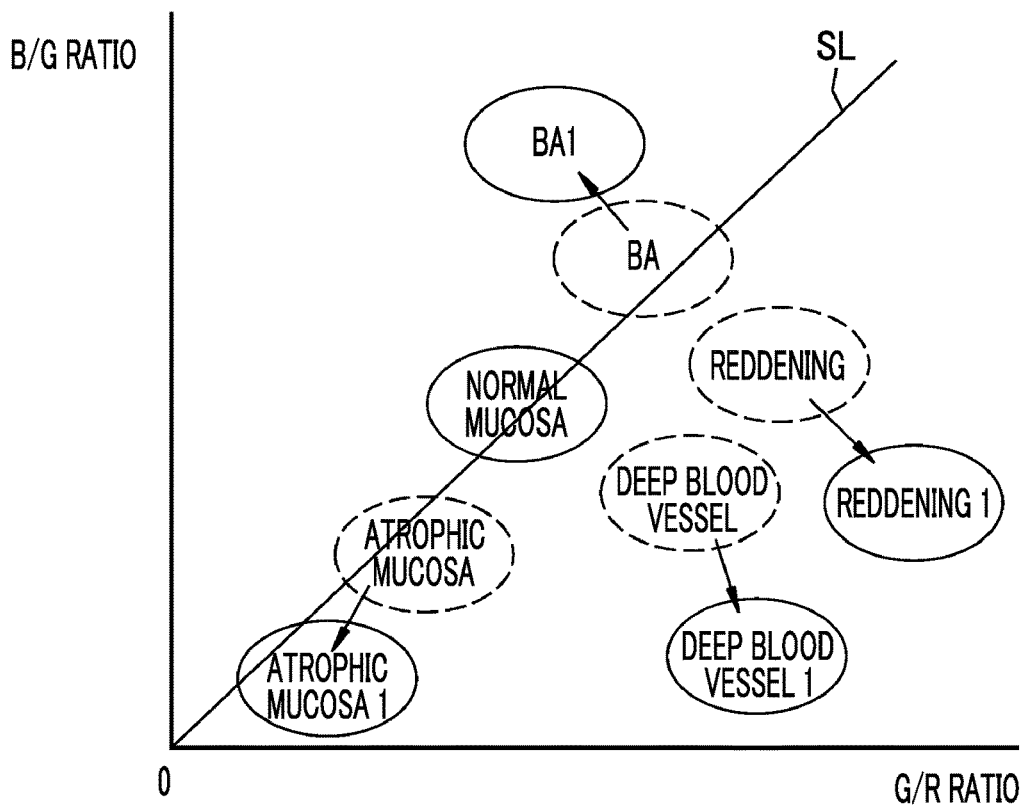
FIG. 13 is an explanatory view showing the distributions of the normal mucosa, the atrophic mucosa, the deep blood vessel, the BA, and reddening before and after the first saturation enhancement processing and the first hue enhancement processing in a signal ratio space.

As described above, with the execution of the first saturation enhancement processing and the first hue enhancement processing, as shown in FIG. 13, the second range (atrophic mucosa 1) of the atrophic mucosa after the first saturation enhancement processing and the first hue enhancement processing is made greater in difference from the first range of the normal mucosa than the second range (dotted line) of the atrophic mucosa before the first saturation enhancement processing and the first hue enhancement processing. Similarly, the deep blood vessel (deep blood vessel 1), the fourth range (BA 1) of the BA, and the fifth range (reddening 1) of reddening after the first saturation enhancement processing and the first hue enhancement processing are made greater in difference from the first range of the normal mucosa than the deep blood vessel (dotted line), the fourth range (dotted line) of the BA, and the fifth range (dotted line) of reddening before the first saturation enhancement processing and the first hue enhancement processing.

Figure 14:
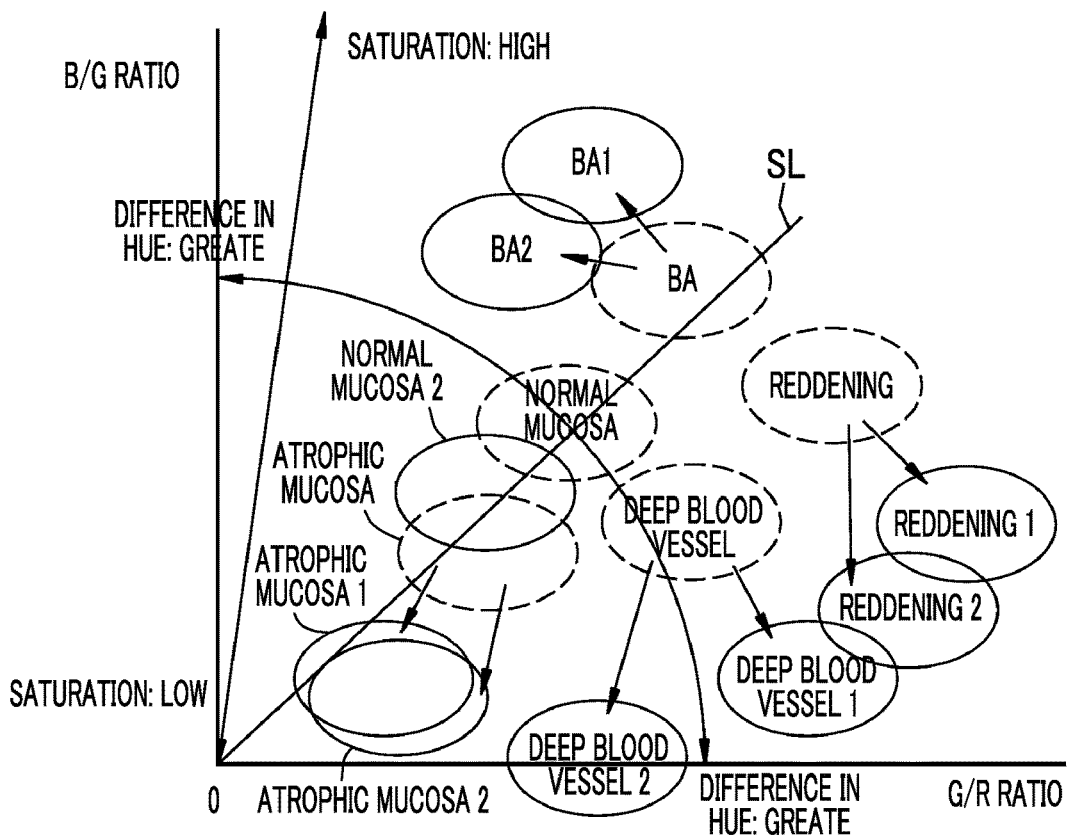
FIG. 14 is an explanatory view showing the distributions of the normal mucosa, the atrophic mucosa, the deep blood vessel, the BA, and reddening before and after the first and second saturation enhancement processing and first and second hue enhancement processing in the signal ratio space.

In a case where the second saturation enhancement processing and the second hue enhancement processing are executed, as shown in FIG. 14, the difference between the first range (normal mucosa 2) of the normal mucosa and each of the third range (deep blood vessel 2) of the deep blood vessel, the fourth range (BA 2) of the BA, and the fifth range (reddening 2) of reddening is made large. It should be noted that the first range (normal mucosa 2) of the normal mucosa after the second saturation enhancement processing and the second hue enhancement processing is made lower in saturation than the first range (normal mucosa) of the normal mucosa before the second saturation enhancement processing and the second hue enhancement processing. Furthermore, the saturation of the second range (atrophic mucosa 2) of the atrophic mucosa is made lower as well.

In addition, the third range (deep blood vessel 2) of the deep blood vessel after the second saturation enhancement processing and the second hue enhancement processing is made lower in saturation than the third range (deep blood vessel 1) of the deep blood vessel after the first saturation enhancement processing and the first hue enhancement processing. Similarly, the fourth range (BA 2) of the BA and the fifth range (reddening 2) of reddening after the second saturation enhancement processing and the second hue enhancement processing is made lower in saturation than the fourth range (BA 1) of the BA and the fifth range (reddening 1) of reddening after the first saturation enhancement processing and the first hue enhancement processing.

The third range (deep blood vessel 2) of the deep blood vessel and the fifth range (reddening 2) of reddening after the second saturation enhancement processing and the second hue enhancement processing are made greater in difference in hue from the first range (normal mucosa 2) of the normal mucosa the third range (deep blood vessel 1) of the deep blood vessel and the fifth range (reddening 1) of reddening after the first saturation enhancement processing and the first hue enhancement processing. The second range (atrophic mucosa 2) of the atrophic mucosa after the second saturation enhancement processing and the second hue enhancement processing is made slightly lower in saturation than the second range (atrophic mucosa 1) of the atrophic mucosa after the first saturation enhancement processing and the first hue enhancement processing. In FIG. 14, in regard to the difference in hue from the first range (normal mucosa 2) of the normal mucosa, the greater the distance from the reference line SL passing through the first range (normal mucosa 2) of the normal mucosa in a radial direction, the greater the difference in hue from the first range (normal mucosa 2) of the normal mucosa.

Even in a case of a feature space (ab space) formed from a* and b* (representing elements a* and b* of tint of a CIE Lab space as color information; the same applies to the following) obtained by Lab-converting the first RGB image signal with a Lab conversion unit, as shown in FIG. 15, the first range of the normal mucosa, the second range of the atrophic mucosa, the third range of the deep blood vessel, the fourth range of the BA, and the fifth range of reddening are distributed like the signal ratio space. Then, with the same method as described above, the saturation enhancement processing for expanding or compressing the radius vector r is executed, and the hue enhancement processing for expanding or compressing the angle θ is executed. The first saturation enhancement processing or the second saturation enhancement processing is executed as the saturation enhancement processing, and the first hue enhancement processing or the second hue enhancement processing is executed as the hue enhancement processing.

The first hue enhancement processing and the first saturation enhancement processing are executed, whereby it is possible to make the difference between the first range of the normal mucosa and each of the second range (atrophic mucosa 1) of the atrophic mucosa, the third range (deep blood vessel 1) of the deep blood vessel, the fourth range (BA 1) of the BA, and the fifth range (reddening 1) of reddening large.

In a case where the second hue enhancement processing and the second saturation enhancement processing are executed, the difference between the first range (normal mucosa 2) of the normal mucosa and each of the third range (deep blood vessel 2) of the deep blood vessel, the fourth range (BA 2) of the BA, and the fifth range (reddening 2) of reddening is made large. It should be noted that the first range (normal mucosa 2) of the normal mucosa after the second saturation enhancement processing and the second hue enhancement processing is made lower in saturation than the first range (normal mucosa 2) of the normal mucosa before the second saturation enhancement processing and the second hue enhancement processing. Furthermore, the saturation of the second range (atrophic mucosa 2) of the atrophic mucosa is made lower as well.

In addition, it is possible to make the third range (deep blood vessel 2) of the deep blood vessel, the fourth range (BA2), and the fifth range (reddening 2) after the second saturation enhancement processing and the second hue enhancement processing are made lower in saturation than the third range (deep blood vessel 1) of the deep blood vessel, the fourth range (BA1), and the fifth range (reddening 1) after the first saturation enhancement processing and the first hue enhancement processing.

Furthermore, it is possible to make the third range (deep blood vessel 2) of the deep blood vessel and the fifth range (reddening 2) of reddening after the second saturation enhancement processing and the second hue enhancement processing are made greater in difference in hue from the first range (normal mucosa 2) of the normal mucosa than the third range (deep blood vessel 1) of the deep blood vessel and the fifth range (reddening 1) of reddening after the first saturation enhancement processing and the first hue enhancement processing. The second range (atrophic mucosa 2) of the atrophic mucosa after the second saturation enhancement processing and the second hue enhancement processing is made greater in difference in hue from the first range (normal mucosa 2) of the normal mucosa than the second range (atrophic mucosa 1) of the atrophic mucosa after the first saturation enhancement processing and the first hue enhancement processing. In FIG. 15, in regard to the difference in hue from the first range of the normal mucosa, the greater the distance from the reference line SL passing through the first range of the normal mucosa in the radial direction, the greater the difference in hue from the first range of the normal mucosa.

Figure 16:
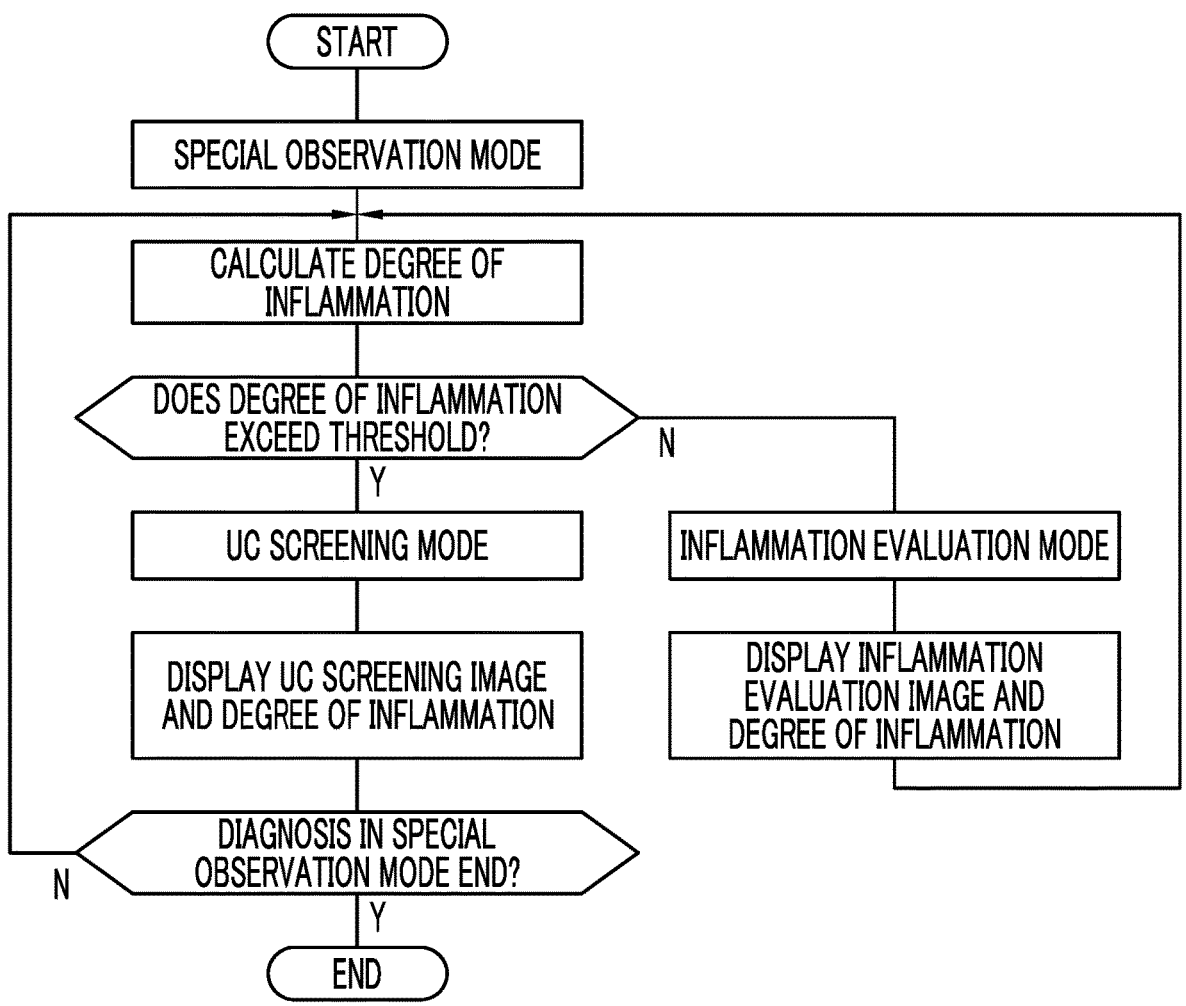
FIG. 16 is a flowchart showing a flow of a special observation mode.

Next, the special observation mode will be described referring to a flowchart of FIG. 16. The mode selection SW 13a is operated to perform switching to the special observation mode. In a case where switching to the special observation mode is performed, the degree of inflammation is calculated based on the image signals before the first saturation enhancement processing and the first hue enhancement processing. In a case where the degree of inflammation does not exceed a threshold value, switching to the inflammation evaluation mode is performed. With this, the inflammation evaluation image is generated and displayed on the monitor 18. The degree of inflammation is displayed on the monitor 18 as well.

In a case where the degree of inflammation exceeds the threshold value, switching to the UC screening mode is performed. In the UC screening mode, the UC screening image is generated. The degree of inflammation and the UC screening image are displayed on the monitor 18. The UC screening image becomes an image in which saturation is more suppressed than the inflammation evaluation image and the hue of the third range of the deep blood vessel is enhanced. In a state in which the degree of inflammation exceeds the threshold value, the UC screening image is continuously displayed, and in a case where the degree of inflammation becomes equal to or less than the threshold value, switching to the inflammation evaluation mode is performed, and switching to the display of the inflammation evaluation image is performed. The above processing is executed until diagnosis in the special observation mode ends (until switching to another observation mode is performed).

Although, in a case where the degree of inflammation exceeds the threshold, switching to the UC screening mode is performed, it is desirable that, in a case where a plurality of frames in which the degree of inflammation exceeds the threshold value are continued, for example, in a case where ten frames in which the degree of inflammation exceeds the threshold value are continued, switching to the UC screening mode is performed. Mode switching is performed in this way, whereby mode switching does not frequently occur. Thus, images with different saturation are not frequently switched. With this, diagnosis is easily performed. Furthermore, although, in a case where the degree of inflammation becomes equal to or less than the threshold value, switching to the inflammation evaluation mode is performed, it is desirable that, in a case where a plurality of frames in which the degree of inflammation becomes equal to or less than the threshold value are continued, switching to the inflammation evaluation mode is performed.

In the above-described embodiment, although switching to the inflammation evaluation mode and the UC screening mode is automatically performed based on the degree of inflammation, switching to the inflammation evaluation mode and the UC screening mode may be manually performed. In this case, as shown in FIG. 17, it is preferable that a setting menu screen is displayed on the screen monitor 18 and a mode is set on the setting menu screen. On the setting menu screen, three modes of the inflammation evaluation mode, the UC screening mode, and the normal mode are selectable. Furthermore, on the setting menu screen, two-screen display of two images among the inflammation evaluation image, the UC screening image, and the normal image can be selected. An operation on the setting menu screen is performed with the console 19 or the like. The setting menu screen may be started by long depression of the mode selection SW 13a or may be started by long depression of a specific button provided in a front panel of the processor device 16.

Figure 18:
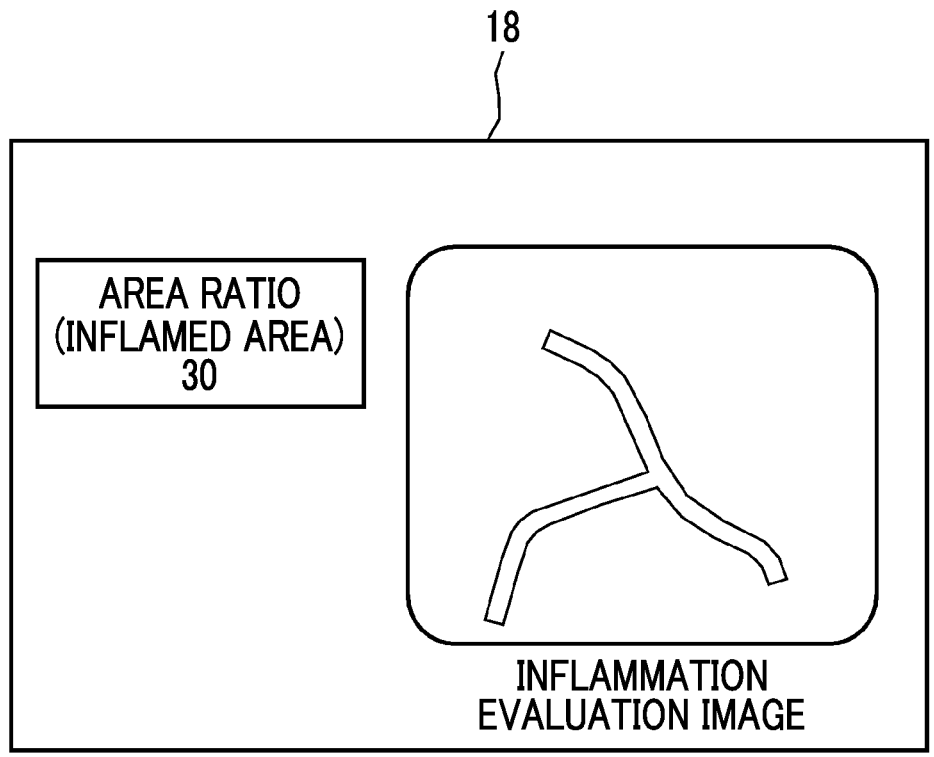
FIG. 18 is an image diagram of a monitor that shows an inflammation evaluation image and an area ratio.
Figure 19:
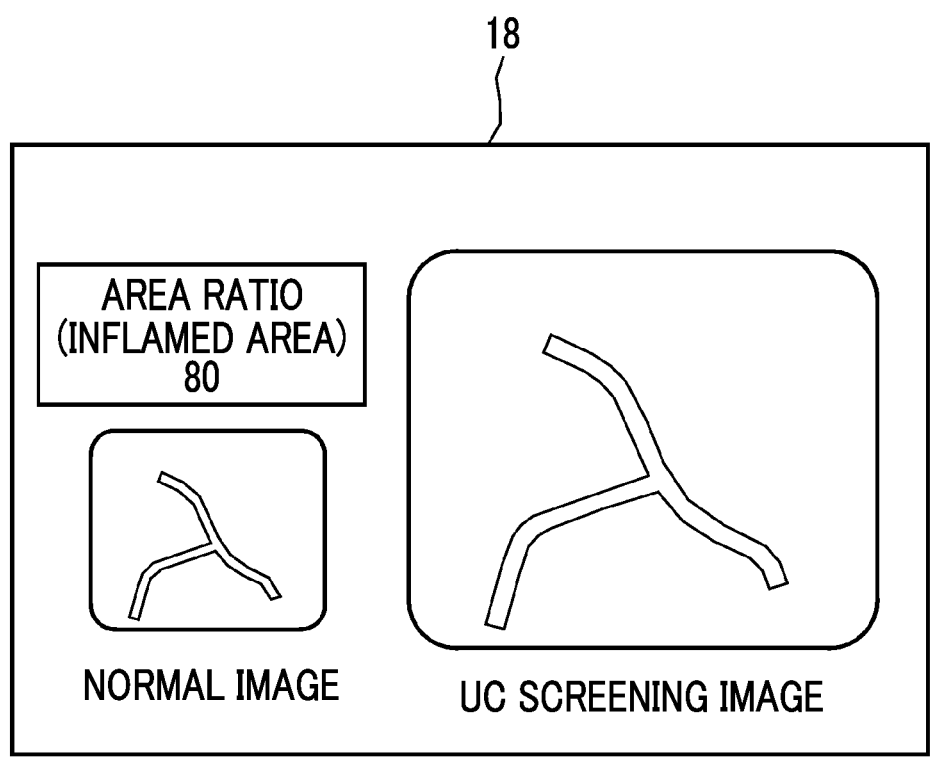
FIG. 19 is an image diagram of a monitor that shows a UC screening image and a normal image displayed on two screens and an area ratio.

For example, in a case where the inflammation evaluation mode is set on the setting menu screen, a box of the inflammation evaluation mode is inverted from white to black on the setting menu screen. Accordingly, as shown in FIG. 18, the inflammation evaluation image is displayed on the monitor 18, and an area ratio is displayed as the degree of inflammation corresponding to the inflammation evaluation image. Furthermore, in a case where the two modes of the UC screening mode and the normal mode are selected on the setting menu screen, a box of the UC screening mode and a box of the normal mode are inverted from white to black. In a case where two-screen is selected, a box of the two-screen is inverted from white to black. In this case, as shown in FIG. 19, the two-screen display of the UC screening image and the normal image is performed. The area ratio is displayed as the degree of inflammation as well.

In the above-described embodiment, although the B/G ratio and the G/R ratio are obtained from the first RGB image signal by the signal ratio calculation unit 72, and the saturation enhancement processing and the hue enhancement processing are executed in the signal ratio space formed from the B/G ratio and the G/R ratio, color information different from the B/G ratio and the G/R ratio may be obtained, and the saturation enhancement processing and the hue enhancement processing may be executed in a feature space formed from the color information.

Figure 20:
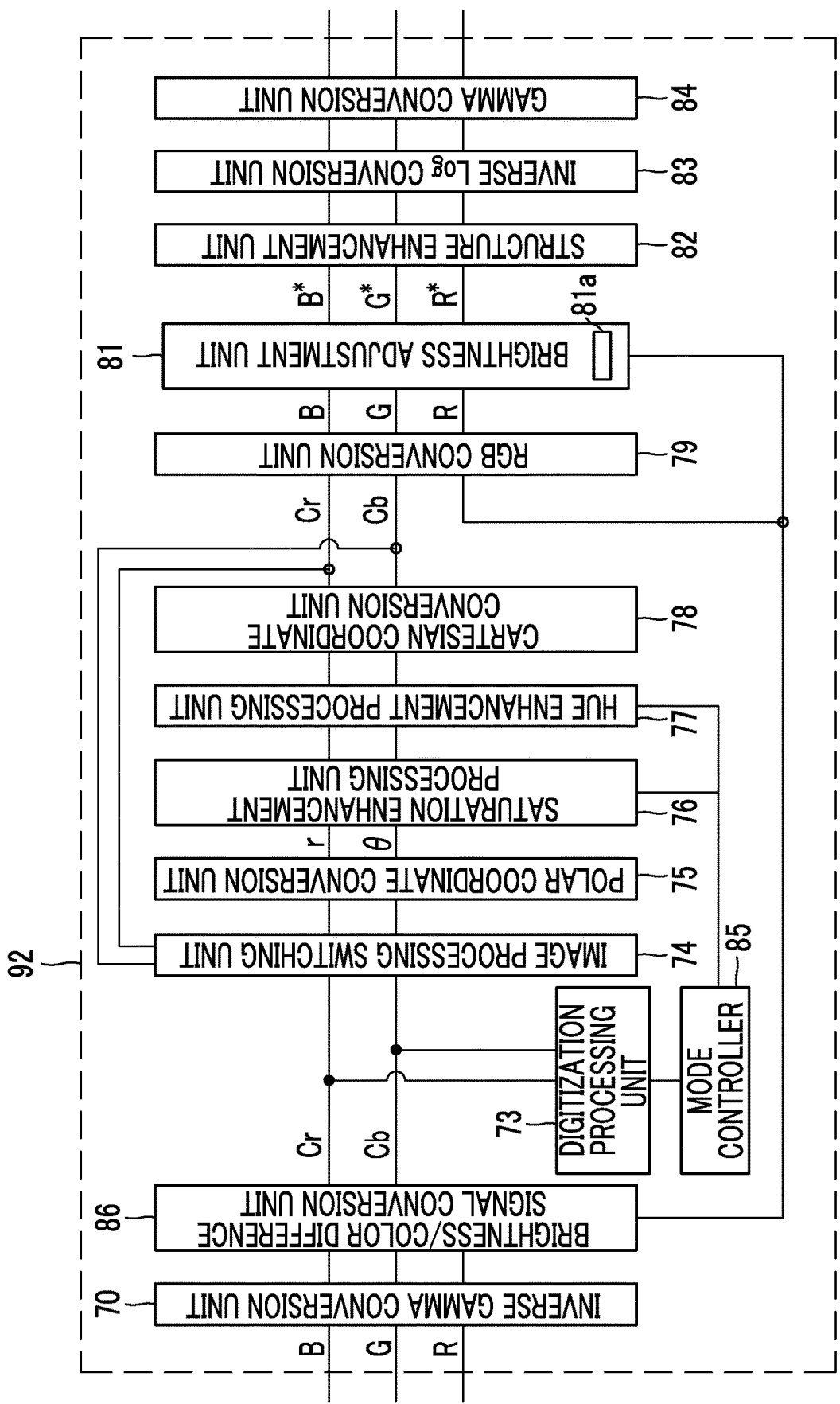
FIG. 20 is a block diagram showing functions of a special image processing unit for use in a case where the feature space is a CrCb space.

For example, color difference signals Cr and Cb may be obtained as the color information, and the saturation enhancement processing and the hue enhancement processing may be executed in a feature space formed from the color difference signals Cr and Cb. In this case, a special image processing unit 92 shown in FIG. 20 is used. The special image processing unit 92 does not comprise the Log conversion unit 71, the signal ratio calculation unit 72, and the inverse Log conversion unit 83 unlike the special image processing unit 64. Instead, the special image processing unit 92 comprises a brightness/color difference signal conversion unit 86. Other configurations of the special image processing unit 92 are the same as those of the special image processing unit 64.

The brightness/color difference signal conversion unit 86 (corresponding to a "color information acquisition unit" of the invention) converts the first RGB image signal to a brightness signal Y and color difference signals Cr and Cb. In the conversion to the color difference signals Cr and Cb, a known conversion expression is used. The color difference signals Cr and Cb are sent to the polar coordinate conversion unit 75. The brightness signal Y is sent to the RGB conversion unit 79 and the brightness adjustment unit 81. In the RGB conversion unit 79, the color difference signals Cr and Cb and the brightness signal Y passing through the Cartesian coordinate conversion unit 78 are converted to a second RGB image signal. In the brightness adjustment unit 81, the pixel values of the second RGB image signal are adjusted using the brightness signal Y as first brightness information Yin and second brightness information obtained by the second brightness information calculation unit 81b as second brightness information Yout. A calculation method of the second brightness information Yout and an adjustment method of the pixel values of the second RGB image signal are the same as in the above-described special image processing unit 64.

Figure 21:
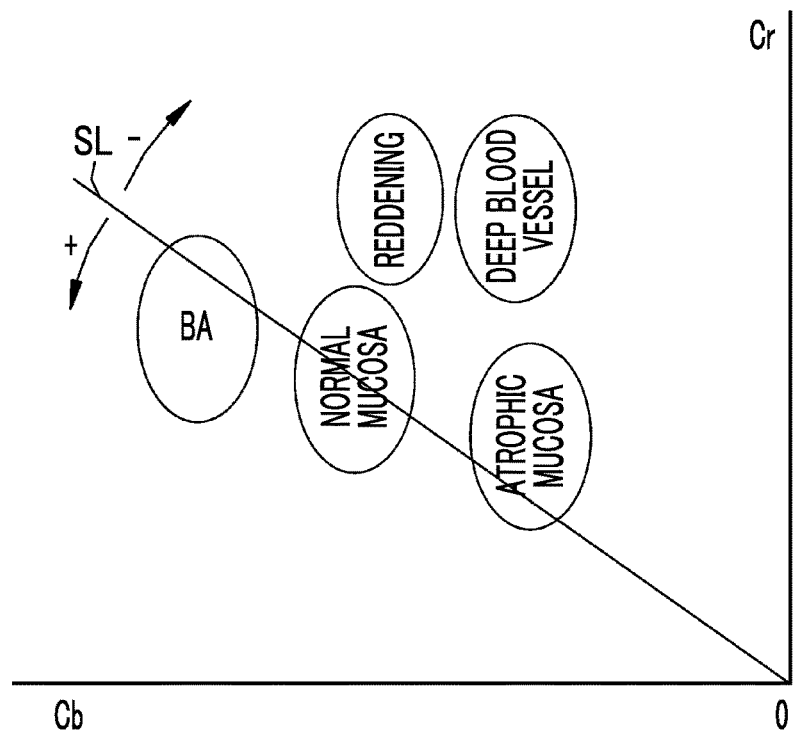
FIG. 21 is an explanatory view showing the ranges of the normal mucosa, the atrophic mucosa, the deep blood vessel, the BA, and reddening that are distributed in the CrCb space.

In the CrCb space formed from the color difference signals Cr and Cb, as shown in FIG. 21, the first range including the normal mucosa is substantially distributed at the center in the second quadrant. The second range including the atrophic mucosa is positioned in the clockwise direction slightly with respect to the reference line SL passing through the first range of the normal mucosa, and is distributed at a position closer to the origin than the first range of the normal mucosa. The third range including the deep blood vessel is distributed in the clockwise direction with respect to the reference line SL. The fourth range including the BA is distributed in the counterclockwise direction slightly with respect to the reference line SL. The fifth range including reddening is distributed in the clockwise direction with respect to the reference line SL. The reference line SL corresponds to the above-described hue reference line SLh. In the CrCb space, the counterclockwise direction with respect to the reference line SL corresponds to the above-described plus direction, and the clockwise direction with respect to the reference line SL corresponds to the above-described minus direction.

Figure 22:
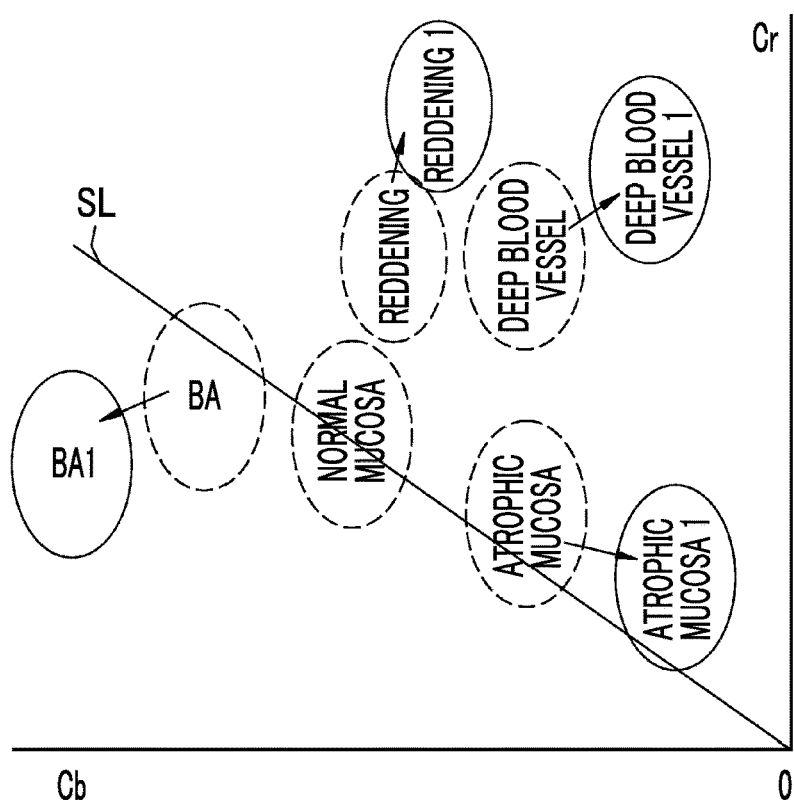
FIG. 22 is an explanatory view showing the distributions of the normal mucosa, the atrophic mucosa, the deep blood vessel, the BA, and reddening before and after the first saturation enhancement processing and the first hue enhancement processing in the CrCb space.

In the CrCb space where the first to fifth ranges are distributed as above, like the signal ratio space, the first saturation enhancement processing for expanding or compressing the radius vector r and the first hue enhancement processing for expanding or compressing the angle θ are executed. With this, as shown in FIG. 22, the second range (atrophic mucosa 1) of the atrophic mucosa after the first saturation enhancement processing and the first hue enhancement processing is made greater in difference from the first range of the normal mucosa than the second range (dotted line) of the atrophic mucosa before the first saturation enhancement processing and the first hue enhancement processing. Similarly, the deep blood vessel (deep blood vessel 1), the fourth range (BA 1) of the BA, and the fifth range (reddening 1) of reddening after the first saturation enhancement processing and the first hue enhancement processing are made greater in difference from the first range of the normal mucosa than the deep blood vessel (dotted line), the fourth range (dotted line) of the BA, and the fifth range (dotted line) of reddening before the first saturation enhancement processing and the first hue enhancement processing.

Figure 23:
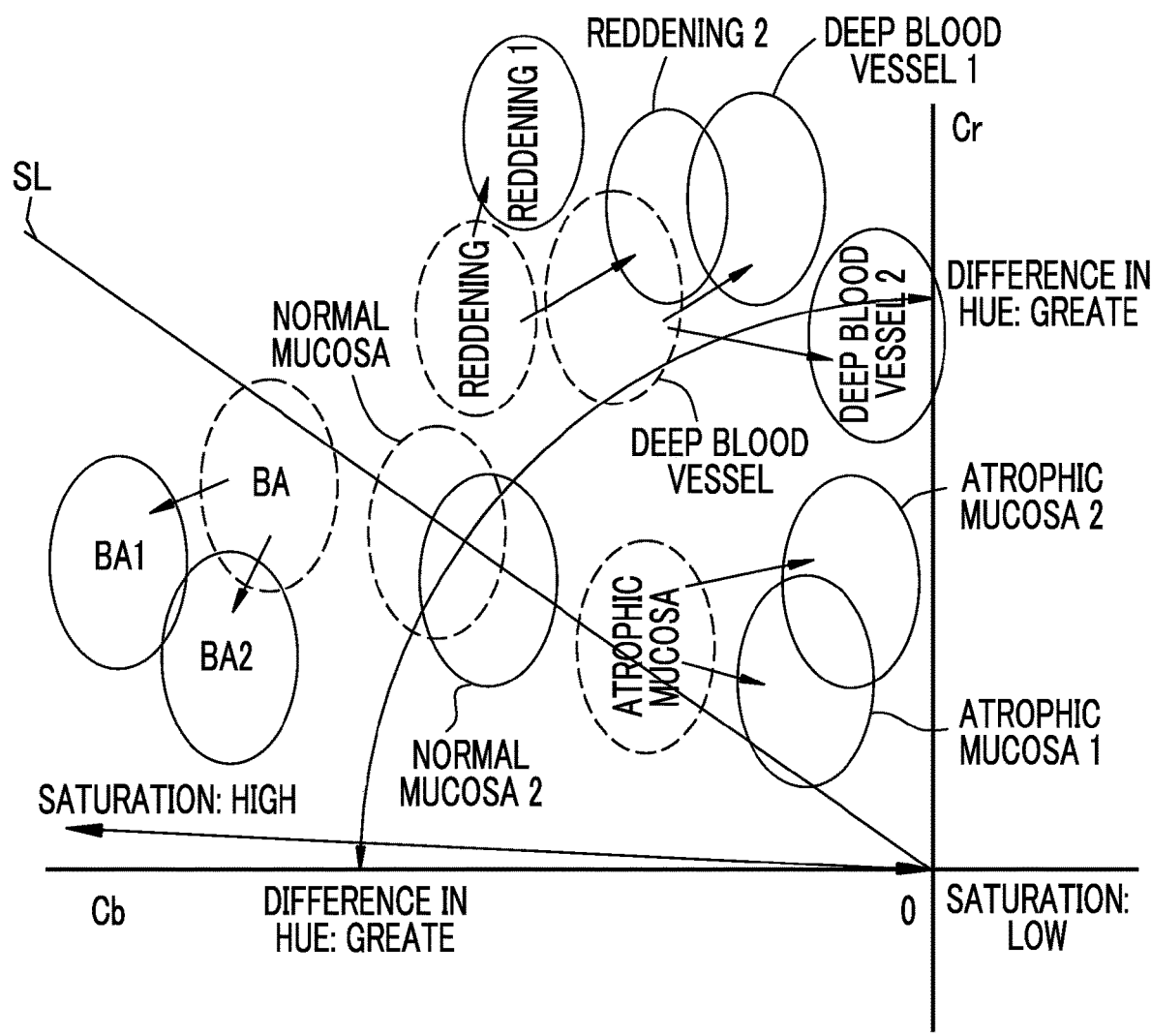
FIG. 23 is an explanatory view showing the distributions of the normal mucosa, the atrophic mucosa, the deep blood vessel, the BA, and reddening before and after the first and second saturation enhancement processing and the first and second hue enhancement processing in the CrCb space.

Furthermore, in the CrCb space where the first to fifth ranges are distributed, like the signal ratio space, the second saturation enhancement processing for expanding or compressing the radius vector r and the second hue enhancement processing for expanding or compressing the angle θ are executed. In a case where the second saturation enhancement processing and the second hue enhancement processing are executed in this way, as shown in FIG. 23, the difference between the first range (normal mucosa 2) of the normal mucosa and each of the third range (deep blood vessel 2) of the deep blood vessel, the fourth range (BA 2) of the BA, and the fifth range (reddening 2) of reddening is made large. It should be noted that the first range (normal mucosa 2) of the normal mucosa after the second saturation enhancement processing and the second hue enhancement processing is made lower in saturation than the first range (normal mucosa) of the normal mucosa before the second saturation enhancement processing and the second hue enhancement processing.

Furthermore, the saturation of the second range (atrophic mucosa 2) of the atrophic mucosa is made lower as well.

In addition, the third range (deep blood vessel 2) of the deep blood vessel after the second saturation enhancement processing and the second hue enhancement processing is made lower in saturation than the third range (deep blood vessel 1) of the deep blood vessel after the first saturation enhancement processing and the first hue enhancement processing. Similarly, the fourth range (BA 2) of the BA and the fifth range (reddening 2) of reddening after the second saturation enhancement processing and the second hue enhancement processing are made lower in saturation than the fourth range (BA 1) of the BA and the fifth range (reddening 1) of reddening after the first saturation enhancement processing and the first hue enhancement processing. Furthermore, the third range (deep blood vessel 2) of the deep blood vessel and the fifth range (reddening 2) of reddening after the second saturation enhancement processing and the second hue enhancement processing are made greater in difference in hue from the first range (normal mucosa 2) of the normal mucosa than the third range (deep blood vessel 1) of the deep blood vessel and the fifth range (reddening 1) of reddening after the first saturation enhancement processing and the first hue enhancement processing.

The second range (atrophic mucosa 2) of the atrophic mucosa after the second saturation enhancement processing and the second hue enhancement processing is made slightly greater in difference in hue from the first range (normal mucosa 2) of the normal mucosa the second range (atrophic mucosa 1) of the atrophic mucosa after the first saturation enhancement processing and the first hue enhancement processing. In FIG. 23, in regard to the difference in hue from the first range of the normal mucosa, the greater the distance from the reference line SL passing through the first range of the normal mucosa in the radial direction, the greater the difference in hue from the first range of the normal mucosa.

Figure 24:
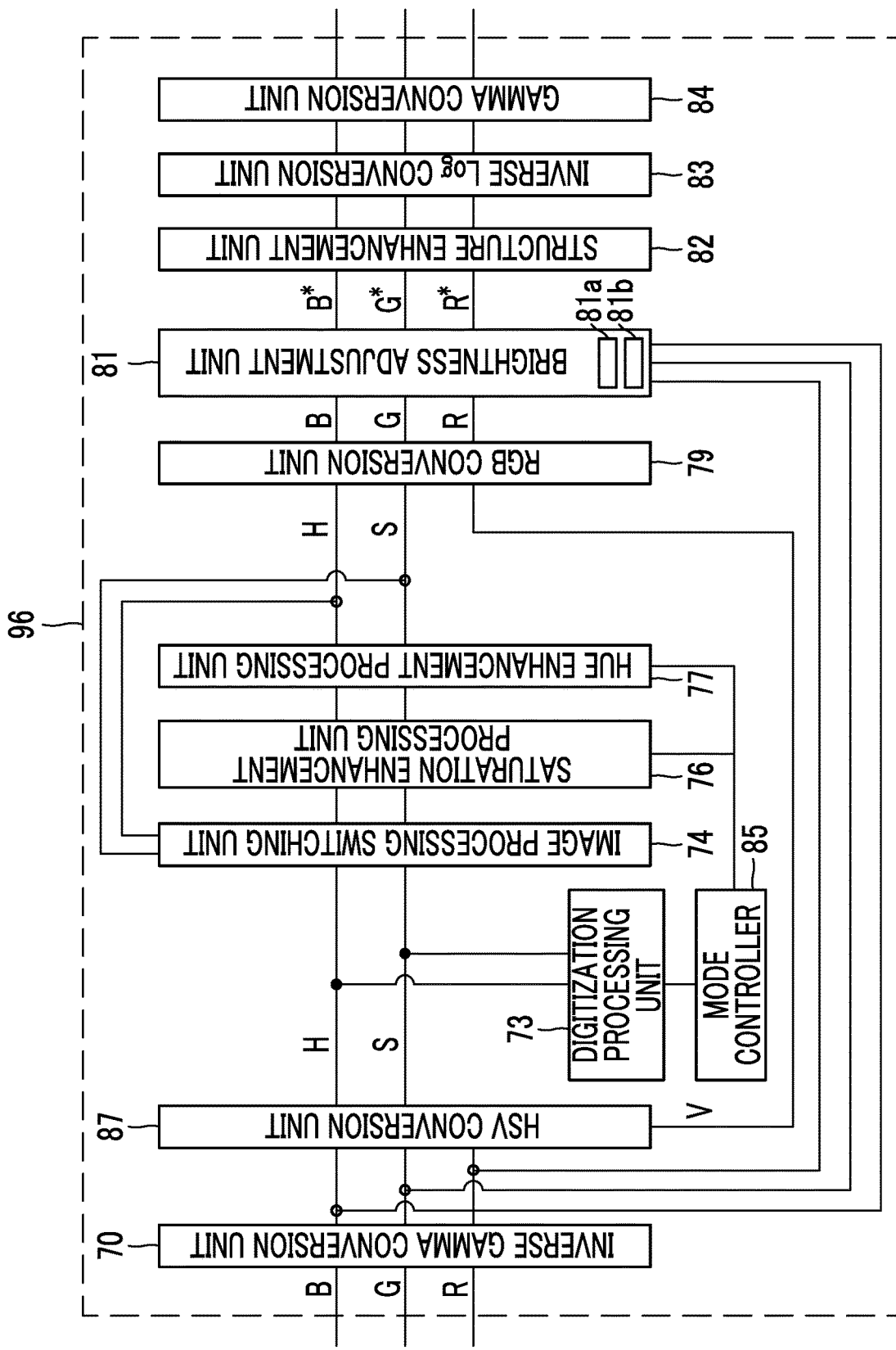
FIG. 24 is a block diagram showing functions of the special image processing unit for use in a case where the feature space is an HS space.

Hue H and saturation S may be obtained as color information, and the saturation enhancement processing and the hue enhancement processing may be executed in an HS space formed from the hue H and the saturation S. In a case where the hue H and the saturation S are used, a special image processing unit 96 shown in FIG. 24 is used. Unlike the special image processing unit 64, the special image processing unit 96 does not comprise the Log conversion unit 71, the signal ratio calculation unit 72, the polar coordinate conversion unit 75, the Cartesian coordinate conversion unit 78, and the inverse Log conversion unit 83. Instead, the special image processing unit 96 comprises an HSV conversion unit 87. Other configurations of the special image processing unit 96 are the same as those of the special image processing unit 64.

The HSV conversion unit 87 (corresponding to a "color information acquisition unit" of the invention) converts the first RGB image signal to hue H, saturation S, and value V. In the conversion to the hue H, the saturation S, and the value V, a known conversion expression is used. The hue H and the saturation S are sent to a parallel shift unit 90. The value V is sent to the RGB conversion unit 79. In the RGB conversion unit 79, the hue H and the saturation S passing through the parallel shift unit 90 and the value V are converted to the second RGB image signal. In the brightness adjustment unit 81, the pixel values of the second RGB image signal are adjusted using the first brightness information Yin obtained by the first brightness information calculation unit 81a and the second brightness information Yout obtained by the second brightness information calculation unit 81b. A calculation method of the first brightness information Yin and the second brightness information Yout and an adjustment method of the pixel values of the second RGB image signal are the same as those in the above-described special image processing unit 64.

Figure 25:
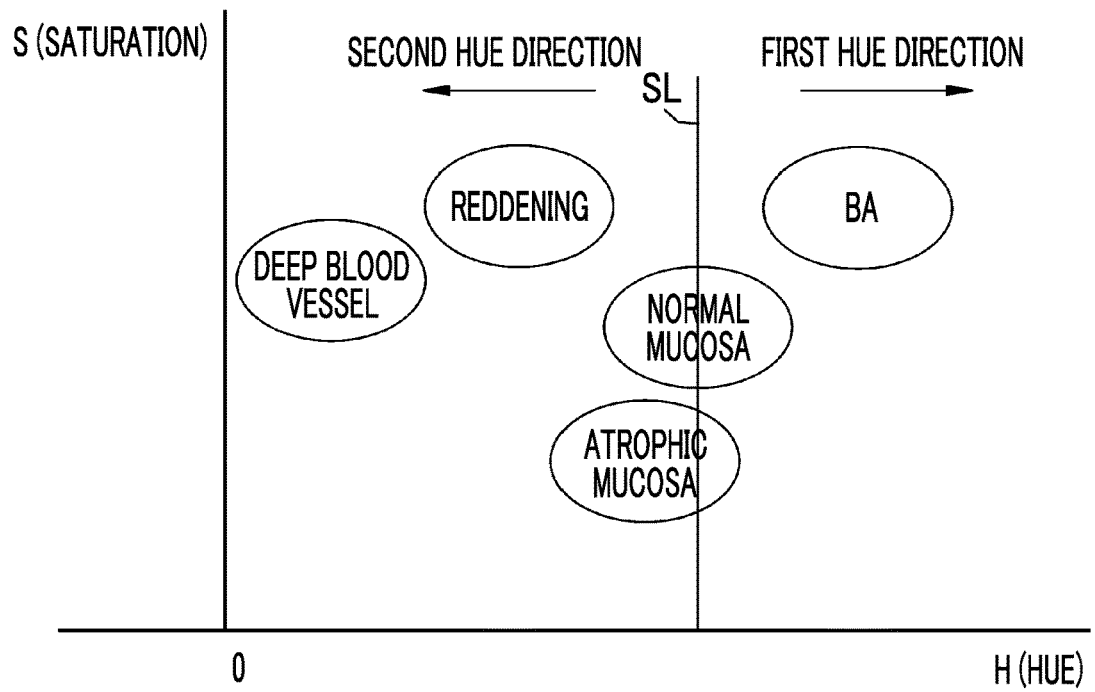
FIG. 25 is an explanatory view showing the ranges of the normal mucosa, the atrophic mucosa, the deep blood vessel, the BA, and reddening that are distributed in the HS space.

In the HS space formed from the hue H and the saturation S, as shown in FIG. 25, the first range including the normal mucosa is distributed on the reference line SL indicating a value of a specific hue. The second range including the atrophic mucosa is distributed at a position of lower saturation than the reference line SL. The fourth range including the BA is distributed at a position in a first hue direction (right side) with respect to the reference line SL with higher saturation than the first range of the normal mucosa. The fifth range including reddening is distributed at a position in a second hue direction (left side) with respect to the reference line SL with higher saturation than the first range of the normal mucosa. The third range including the deep blood vessel is distributed at a position with higher saturation than the first range of the normal mucosa and lower saturation than the fourth range of the BA or the fifth range of reddening. The third range of the deep blood vessel is distributed at a position in the second hue direction (left side) different from the first hue direction with respect to the reference line SL. The distance in the hue direction between the fifth range of reddening and the reference line SL becomes smaller than a distance between the third range of the deep blood vessel and the reference line SL.

As described above, in the first saturation enhancement processing and the first hue enhancement processing in the HS space where the first to fifth ranges are distributed, processing for shifting the second to fifth ranges in parallel is executed without expanding or compressing the radius vector r and the angle θ as in the signal ratio space and the CrCb space. The saturation enhancement processing unit 76 executes, as the first saturation enhancement processing, processing for shifting the second range of the atrophic mucosa in a saturation direction in parallel to become low saturation. On the other hand, it is preferable that the saturation enhancement processing unit 76 executes, as the first saturation enhancement processing, processing for shifting the third range of the deep blood vessel, the fourth range of the BA, and the fifth range of reddening in the saturation direction in parallel to become high saturation.

The third to fifth ranges may be shifted in parallel to become low saturation. Furthermore, the hue enhancement processing unit 77 executes, as the first hue enhancement processing, processing for shifting the third range of the deep blood vessel, the fourth range of the BA, and the fifth range of reddening in the hue direction in parallel to be distant from the first range of the normal mucosa. The hue enhancement processing unit 77 may execute, as the first hue enhancement processing, processing for shifting the second range of the atrophic mucosa in the hue direction.

Figure 26:
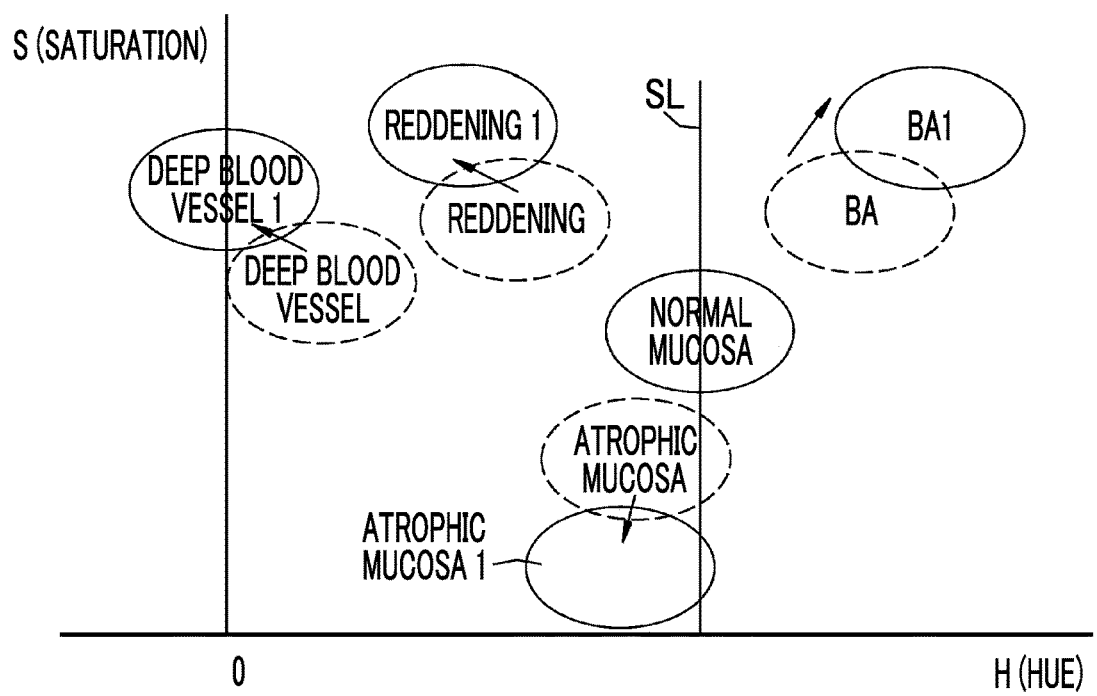
FIG. 26 is an explanatory view showing the distributions of the normal mucosa, the atrophic mucosa, the deep blood vessel, the BA, and reddening before and after the first saturation enhancement processing and the first hue enhancement processing in the HS space.

With the execution of the first saturation enhancement processing and the first hue enhancement processing described above, as shown in FIG. 26, the second range (atrophic mucosa 1) of the atrophic mucosa after the first saturation enhancement processing and the first hue enhancement processing is made greater in difference from the first range of the normal mucosa than the second range (dotted line) of the atrophic mucosa before the first saturation enhancement processing and the first hue enhancement processing. Similarly, the deep blood vessel (deep blood vessel 1), the fourth range (BA 1) of the BA, and the fifth range (reddening 1) of reddening after the first saturation enhancement processing and the first hue enhancement processing are made greater in difference from the first range of the normal mucosa than the deep blood vessel (dotted line), the fourth range (dotted line) of the BA, and the fifth range (dotted line) of reddening before the first saturation enhancement processing and the first hue enhancement processing.

Even as the second saturation enhancement processing and the second hue enhancement processing in the HS space, processing for shifting the second to fifth ranges in parallel is executed. It should be noted that, in a case where the second saturation enhancement processing is executed, it is preferable that the amount of shift of an observation target range included in the high saturation range in the saturation direction is made smaller than in a case where the first saturation enhancement processing is executed. Specifically, for the third range of the deep blood vessel, the fourth range of the BA, and the fifth range of reddening included in the high saturation range, the amount of shift in the saturation direction is made smaller than in the first saturation enhancement processing. Furthermore, in a case where the second hue enhancement processing is executed, it is preferable that the amount of shift of the third range of the deep blood vessel in the hue direction is made smaller than in the first hue enhancement processing.

Figure 27:
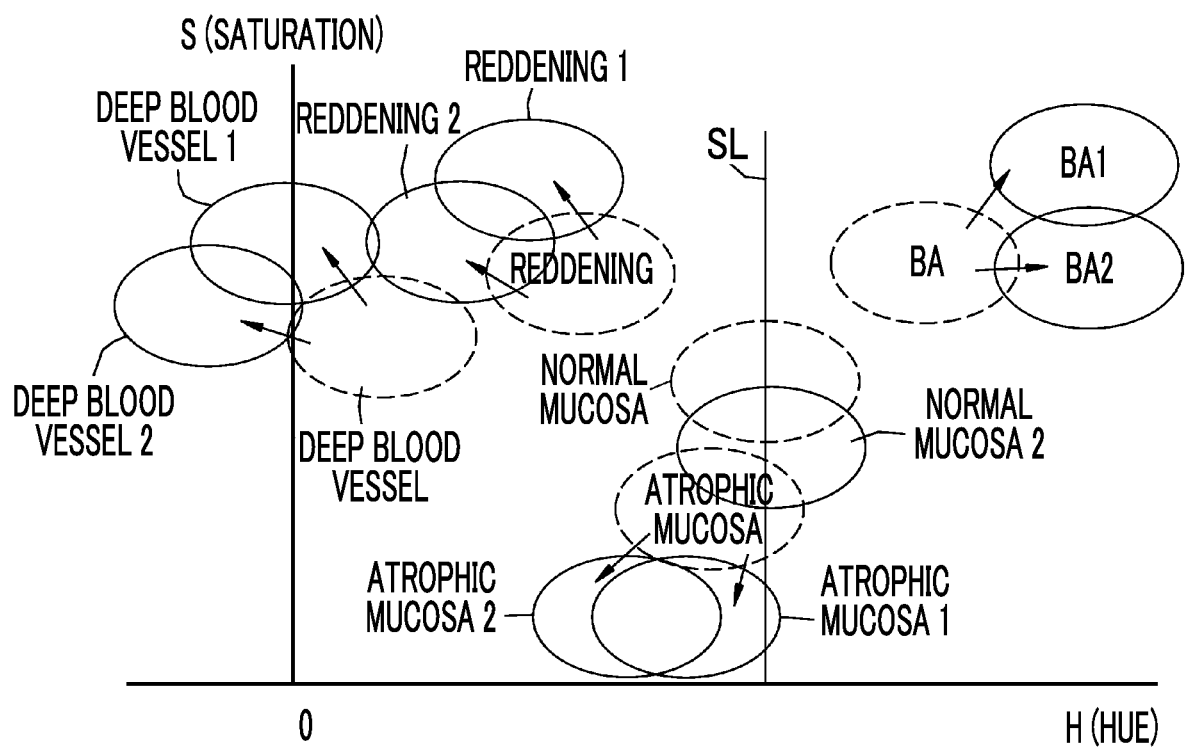
FIG. 27 is an explanatory view the distributions of the normal mucosa, the atrophic mucosa, the deep blood vessel, the BA, and reddening before and after the first and second saturation enhancement processing and the first and second hue enhancement processing in the HS space.

In a case where the second saturation enhancement processing and the second hue enhancement processing are executed in this way, as shown in FIG. 27, the difference between the first range (normal mucosa 2) of the normal mucosa and each of the third range (deep blood vessel 2) of the deep blood vessel, the fourth range (BA 2) of the BA, and the fifth range (reddening 2) of reddening is made large. It should be noted that the first range (normal mucosa 2) of the normal mucosa after the second saturation enhancement processing and the second hue enhancement processing is made lower in saturation than the first range (normal mucosa) of the normal mucosa before the second saturation enhancement processing and the second hue enhancement processing. Furthermore, the saturation of the second range (atrophic mucosa 2) of the atrophic mucosa is made lower as well.

In addition, the third range (deep blood vessel 2) of the deep blood vessel after the second saturation enhancement processing and the second hue enhancement processing is made lower in saturation than the third range (deep blood vessel 1) of the deep blood vessel after the first saturation enhancement processing and the first hue enhancement processing. Similarly, the fourth range (BA 2) of the BA and the fifth range (reddening 2) of reddening after the second saturation enhancement processing and the second hue enhancement processing are made lower in saturation than the fourth range (BA 1) of the BA and the fifth range (reddening 1) of reddening after the first saturation enhancement processing and the first hue enhancement processing.

Furthermore, the third range (deep blood vessel 2) of the deep blood vessel and the fifth range (reddening 2) of reddening after the second saturation enhancement processing and the second hue enhancement processing are made greater in difference in hue from the first range (normal mucosa 2) of the normal mucosa than the third range (deep blood vessel 1) of the deep blood vessel, and the fifth range (reddening 1) of reddening after the first saturation enhancement processing and the first hue enhancement processing. The second range (atrophic mucosa 2) of the atrophic mucosa after the second saturation enhancement processing and the second hue enhancement processing is made slightly greater in difference in hue from the first range (normal mucosa 2) of the normal mucosa than the second range (atrophic mucosa 1) of the atrophic mucosa after the first saturation enhancement processing and the first hue enhancement processing. In FIG. 27, the difference in hue from the first range of the normal mucosa is represented by the distance from the first range of the normal mucosa in the hue direction. Specifically, the greater the distance from the reference line SL, that is, the greater the distance from the reference line SL in the hue direction, the greater the difference in hue from the first range of the normal mucosa.

Second Embodiment

In a second embodiment, an observation target is illuminated using a laser beam source and a phosphor, instead of the LEDs 20a to 20d of the four colors shown in the first embodiment. Other than that, the components are the same as those in the first embodiment.

Figure 28:
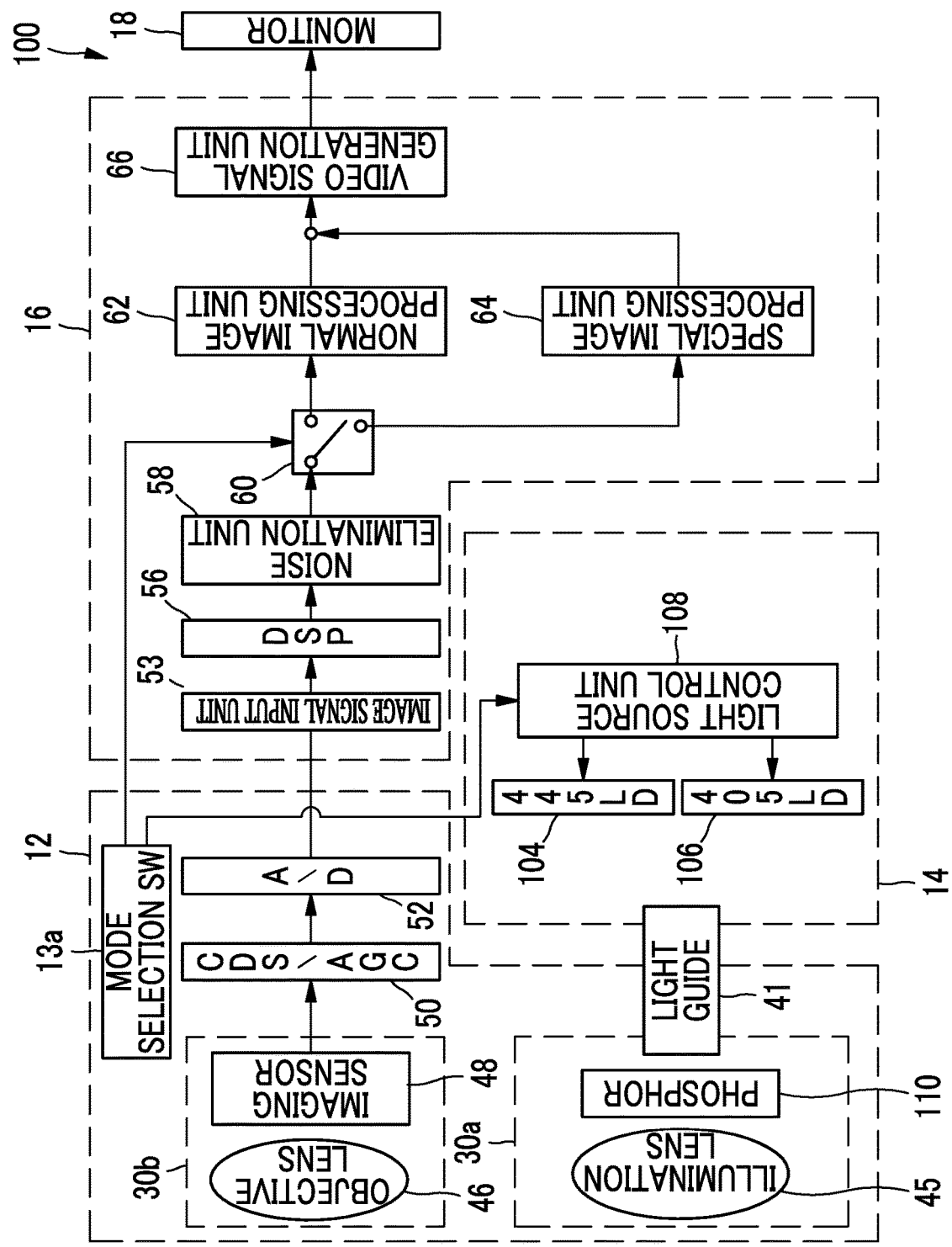
FIG. 28 is a block diagram showing functions of an endoscope system of a second embodiment.

As shown in FIG. 28, in an endoscope system 100 of the second embodiment, a light source device 14 is provided with, instead of the LEDs 20a to 20d of the four colors, a blue laser beam source (in FIG. 36, denoted as "445LD") 104 that emits a blue laser beam having a center wavelength of 445±10 nm, and a blue-violet laser beam source (in FIG. 36, denoted as "405LD") 106 that emits a blue-violet laser beam having a center wavelength of 405±10 nm. Light emission from semiconductor light emitting elements of the beam sources 104 and 106 is individually controlled by a light source controller 108, and the light quantity ratio between emitted light from the blue laser beam source 104 and emitted light of the blue-violet laser beam source 106 is freely changeable.

The light source controller 108 drives the blue laser beam source 104 in a case of the normal observation mode. In contrast, in the special observation mode, both of the blue laser beam source 104 and the blue-violet laser beam source 106 are driven, and a light emission ratio of the blue laser beam is controlled so as to be greater than a light emission ratio of the blue-violet laser beam. The laser beams emitted from the beam sources 104 and 106 are incident on the light guide 41 through optical members (all not shown), such as a condenser lens, an optical fiber, or a multiplexer.

It is preferable that the half width of the blue laser beam or the blue-violet laser beam is about ±10 nm. For the blue laser beam source 104 and the blue-violet laser beam source 106, a broad-area type InGaN-based laser diode may be used, or an InGaNAs-based laser diode or a GaNAs-based laser diode may be used. As the light sources described above, a light emitting element, such as a light emitting diode, may be used.

The illumination optical system 30a is provided with a phosphor 110 on which the blue laser beam or the blue-violet laser beam from the light guide 41 is incident, in addition to the illumination lens 45. The phosphor 110 is irradiated with the blue laser beam, whereby fluorescence is emitted from the phosphor 110. A part of the blue laser beams is transmitted through the phosphor 110. The blue-violet laser beam is transmitted through the phosphor 110 without exciting the phosphor 110. The inside of the subject is irradiated with light emitted from the phosphor 110 through the illumination lens 45.

Figure 29:
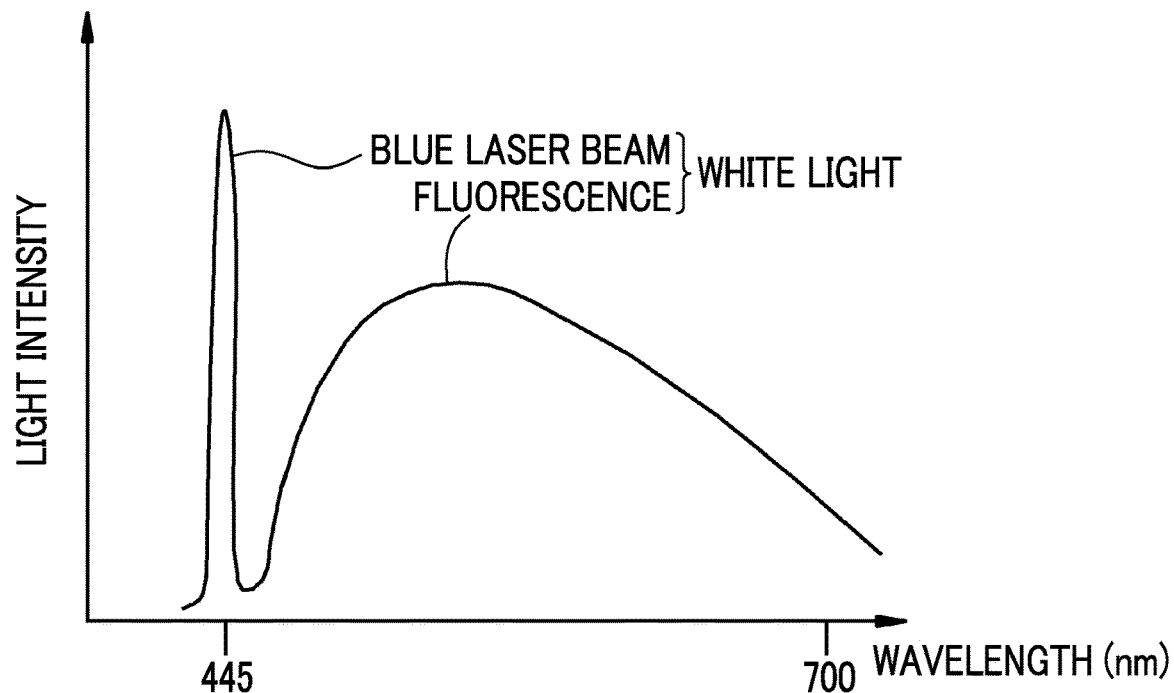
FIG. 29 is a graph showing a light emission spectrum of white light.
Figure 30:
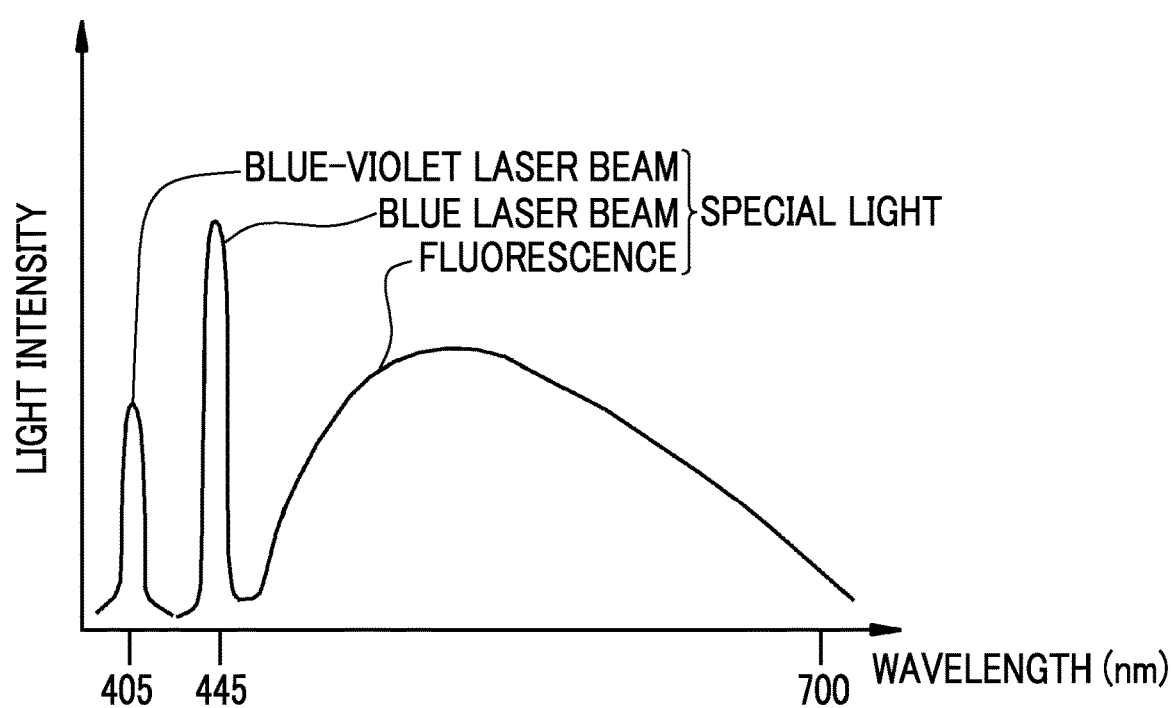
FIG. 30 is a graph showing a light emission spectrum of special light.

In the normal observation mode, since the blue laser beam is mostly incident on the phosphor 110, the observation target is irradiated with white light that is the combination of the blue laser beam and the fluorescence emitted from the phosphor 110 excited by the blue laser beam as shown in FIG. 29. In the special observation mode, since both of the blue-violet laser beam and the blue laser beam are incident on the phosphor 110, the inside of the subject is irradiated with special light that is the combination of the blue-violet laser beam, the blue laser beam, and the fluorescence emitted from the phosphor 110 excited by the blue laser beam as shown in FIG. 30.

It is preferable that the phosphor 110 includes a plurality of phosphors (for example, phosphors, such as YAG-based phosphors or $BaMgAl_{10}O_{17}$ (BAM)) that absorb a part of the blue laser beams and is excited to emit green to yellow colors. As in this configuration example, in a case where a semiconductor light emitting element is used as the excitation light source of the phosphor 110, white light with high intensity is obtained with high light emission efficiency, and it is possible to easily adjust the intensity of white light and to minimize changes in color temperature and chromaticity of white light.

Third Embodiment

In a third embodiment, an observation target is illuminated using a broadband light source, such as a Xenon lamp, and a rotary filter, instead of the LEDs 20a to 20d of the four colors shown in the first embodiment. The observation target is imaged with a monochrome imaging sensor, instead of the color imaging sensor 48. Other than that, the components are the same as those in the first embodiment.

Figure 31:
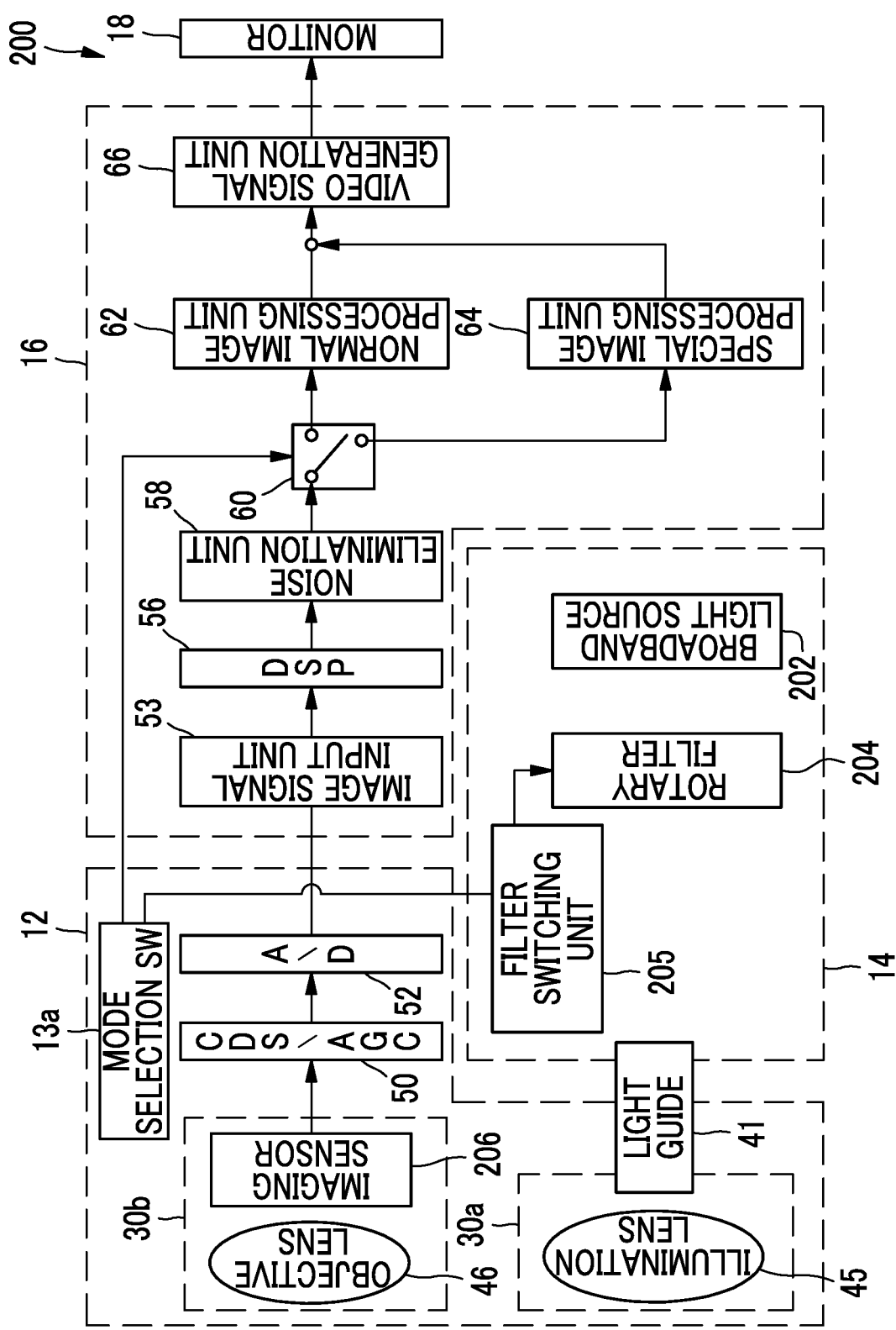
FIG. 31 is a block diagram showing functions of an endoscope system of a third embodiment.

As shown in FIG. 31, a light source device 14 of an endoscope system 200 of the third embodiment is provided with a broadband light source 202, a rotary filter 204, and a filter switching unit 205, instead of the LEDs 20a to 20d of the four colors. The imaging optical system 30b is provided with a monochrome imaging sensor 206 with no color filters, instead of the color imaging sensor 48.

The broadband light source 202 is a Xenon lamp, a white LED, or the like, and emits white light having a wavelength band from blue to red. The rotary filter 204 comprises an internal filter 208 for a normal observation mode and an external filter 209 for a special observation mode (see FIG. 32). The filter switching unit 205 moves the rotary filter 204 in a radius direction, inserts the filter 208 for a normal observation mode of the rotary filter 204 into the optical path of white light when the normal observation mode is set by the mode selection SW 13a, and inserts the filter 209 for a special observation mode of the rotary filter 204 into the optical path of white light when the special observation mode is set.

Figure 32:
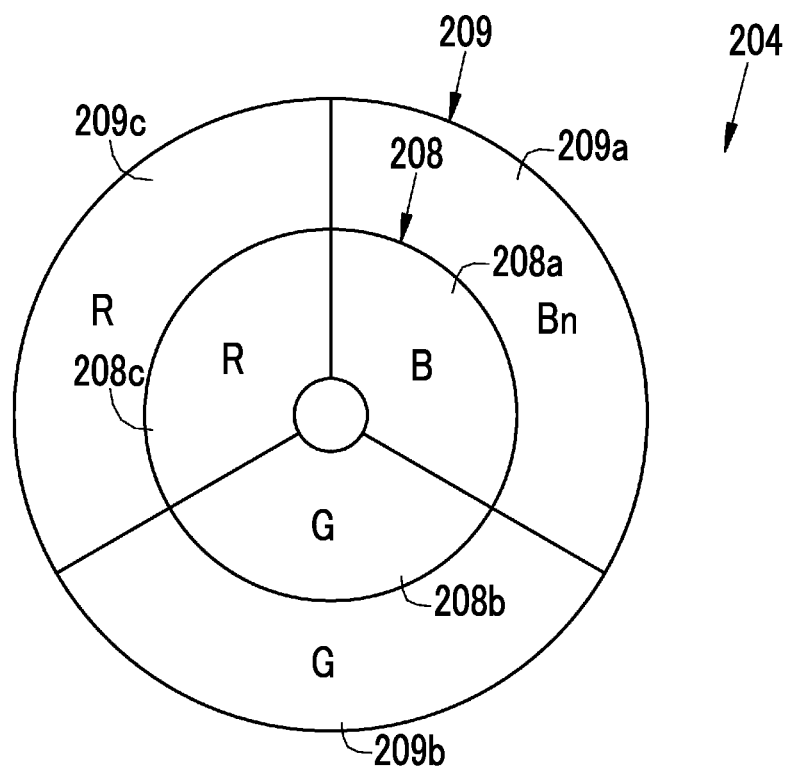
FIG. 32 is a plan view showing a rotary filter.

As shown in FIG. 32, the filter 208 for a normal observation mode is provided with, in a circumferential direction, a B filter 208a that transmits blue light from white light, a G filter 208b that transmits green light from white light, and an R filter 208c that transmits red light from white light. Accordingly, in the normal observation mode, the rotary filter 204 rotates, whereby the observation target is alternately irradiated with blue light, green light, and red light.

The filter 209 for a special observation mode is provided with, in a circumferential direction, a Bn filter 209a that transmits blue narrowband light having a specific wavelength from white light, a G filter 209b that transmits green light from white light, and an R filter 209c that transmits red light from white light. Accordingly, in the special observation mode, the rotary filter 204 rotates, whereby the observation target is alternately irradiated with blue narrowband light, green light, and red light.

In the endoscope system 200, in the normal observation mode, the inside of the subject is imaged by the monochrome imaging sensor 206 each time the observation target is irradiated with blue light, green light, and red light. With this, image signals of three colors of RGB are obtained. A normal image is generated based on the image signals of RGB by the same method as in the foregoing first embodiment.

In the special observation mode, the inside of the subject is imaged by the monochrome imaging sensor 206 each time the observation target is irradiated with blue narrowband light, green light, and red light. With this, a Bn image signal, a G image signal, and an R image signal are obtained. A special image is generated based on the Bn image signal, the G image signal, and the R image signal. In generating the special image, the Bn image signal is used, instead of the B image signal. Except for this, the generation of the special image is performed by the same method as in the first embodiment.

Fourth Embodiment

In a fourth embodiment, an RGB image signal necessary for generating a normal image or a special image is acquired using a swallow-type capsule endoscope, instead of the insertion-type endoscope 12 and the light source device 14.

Figure 33:
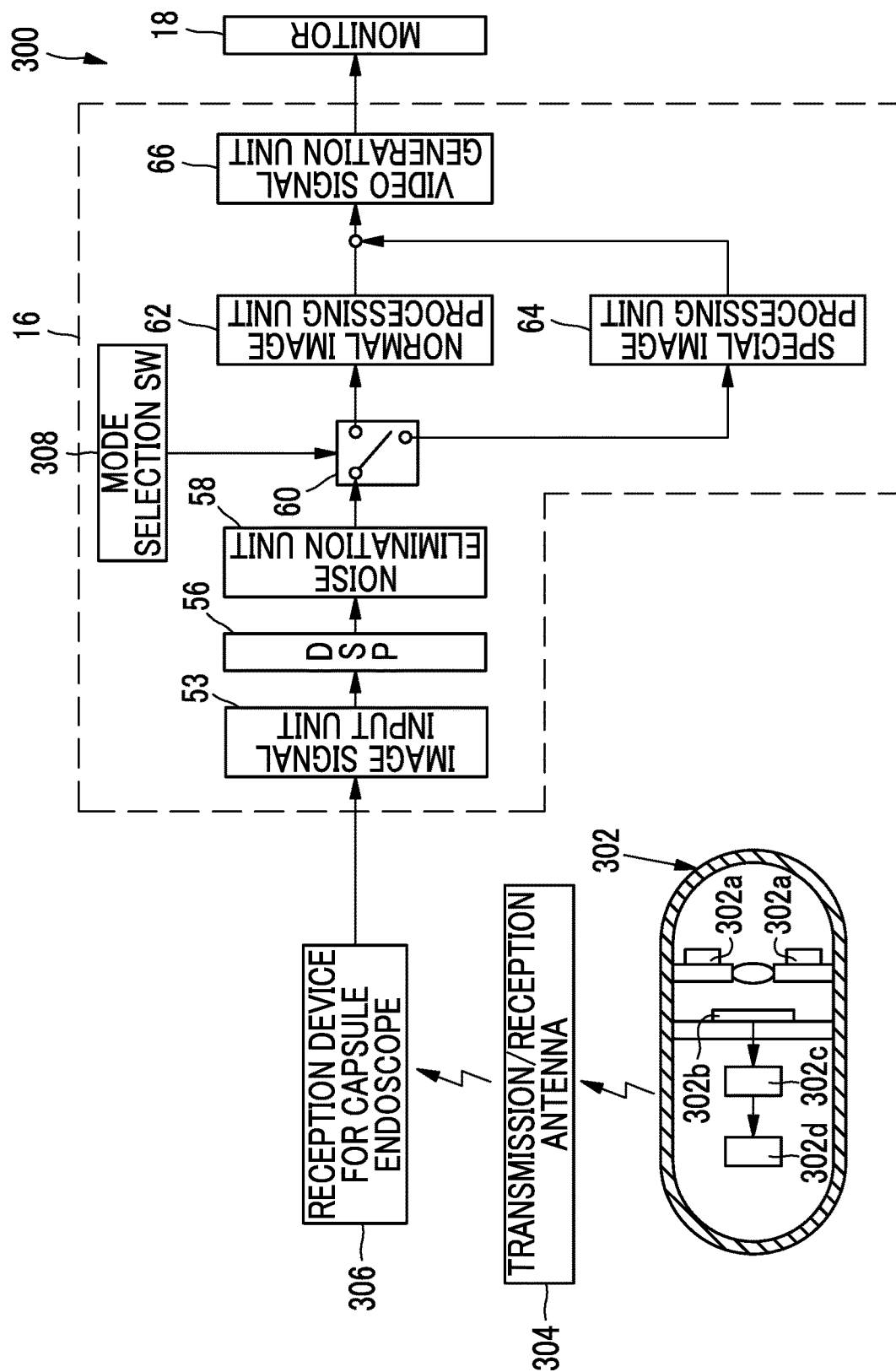
FIG. 33 is a diagram showing functions of a capsule endoscope system of a fourth embodiment.

As shown in FIG. 33, a capsule endoscope system 300 of the fourth embodiment comprises a capsule endoscope 302, a transmission/reception antenna 304, a reception device 306 for a capsule endoscope, the processor device 16, and the monitor 18. The capsule endoscope 302 comprises an LED 302a, an imaging sensor 302b, an image processing unit 302c, and a transmission antenna 302d. While the processor device 16 is the same as that in the first embodiment, in the fourth embodiment, a mode selection SW 308 for switching between the normal observation mode and the special observation mode is newly provided.

A plurality of LEDs 302a that emit white light are provided in the capsule endoscope 302. As the LEDs 302a, it is preferable to use a white LED or the like comprising a blue light source and a phosphor that performs wavelength conversion of light from the blue light source to emit fluorescence. A laser diode (LD) may be used, instead of the LED. The observation target is illuminated with white light emitted from the LEDs 302a.

The imaging sensor 302b is a color imaging sensor, images the observation target illuminated with white light, and outputs an RGB image signal. As the imaging sensor 302b, it is preferable to use a charge coupled device (CCD) imaging sensor or a complementary metal-oxide semiconductor (CMOS) imaging sensor. The RGB image signal output from the imaging sensor 302b is subjected to processing for converting the RGB image signal to a signal to be transmitted through the transmission antenna 302d in the image processing unit 302c. The RGB image signal having passed through the image processing unit 302c is transmitted from the transmission antenna 302d to the transmission/reception antenna 304 in a wireless manner.

The transmission/reception antenna 304 is affixed to the subject's body, and receives the RGB image signal from the transmission antenna 302d. The transmission/reception antenna 304 transmits the received RGB image signal to the reception device 306 for a capsule endoscope in a wireless manner. The reception device 306 for a capsule endoscope is connected to the image signal input unit 53 of the processor device 16, and transmits the RGB image signal from the transmission/reception antenna 304 to the image signal input unit 53.

Figure 34:
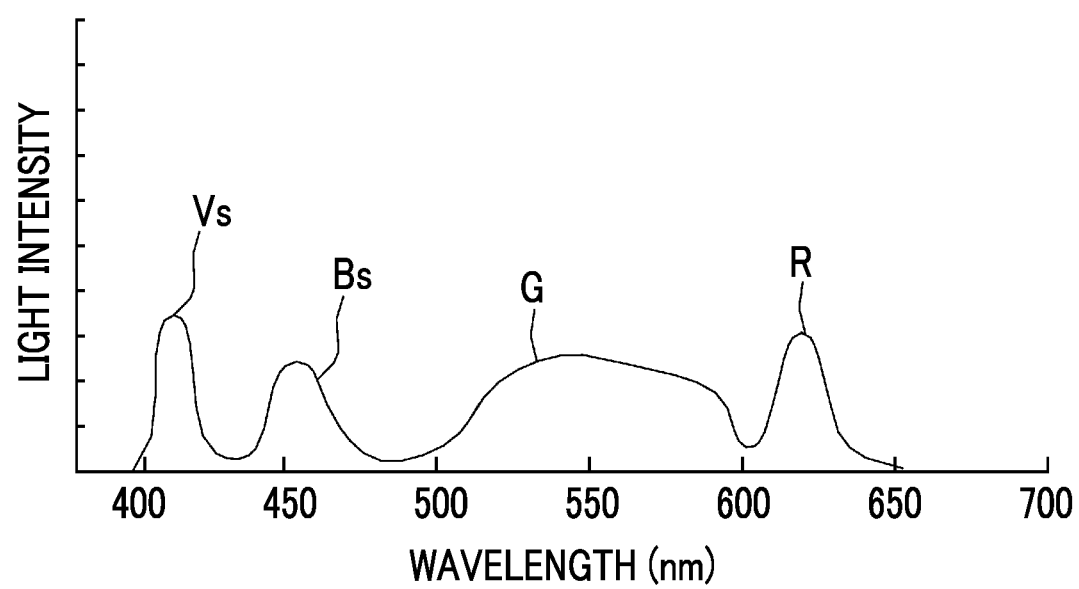
FIG. 34 is a graph showing light emission spectra of violet light V, blue light B, green light G, and red light R different from FIG. 3.

In the foregoing embodiments, although light of the four colors having the light emission spectra shown in FIG. 3 is used, the light emission spectra is not limited thereto. For example, as shown in FIG. 34, green light G and red light R may have the same spectra as those shown in FIG. 3, and violet light Vs may be light having a center wavelength of 410 nm to 420 nm and a wavelength range slightly shifted to a longer wavelength side than violet light V of FIG. 3. Blue light Bs may be light having a center wavelength of 445 nm to 460 nm and a wavelength range slightly shifted to a shorter wavelength side than blue light B of FIG. 3.

Figure 35:
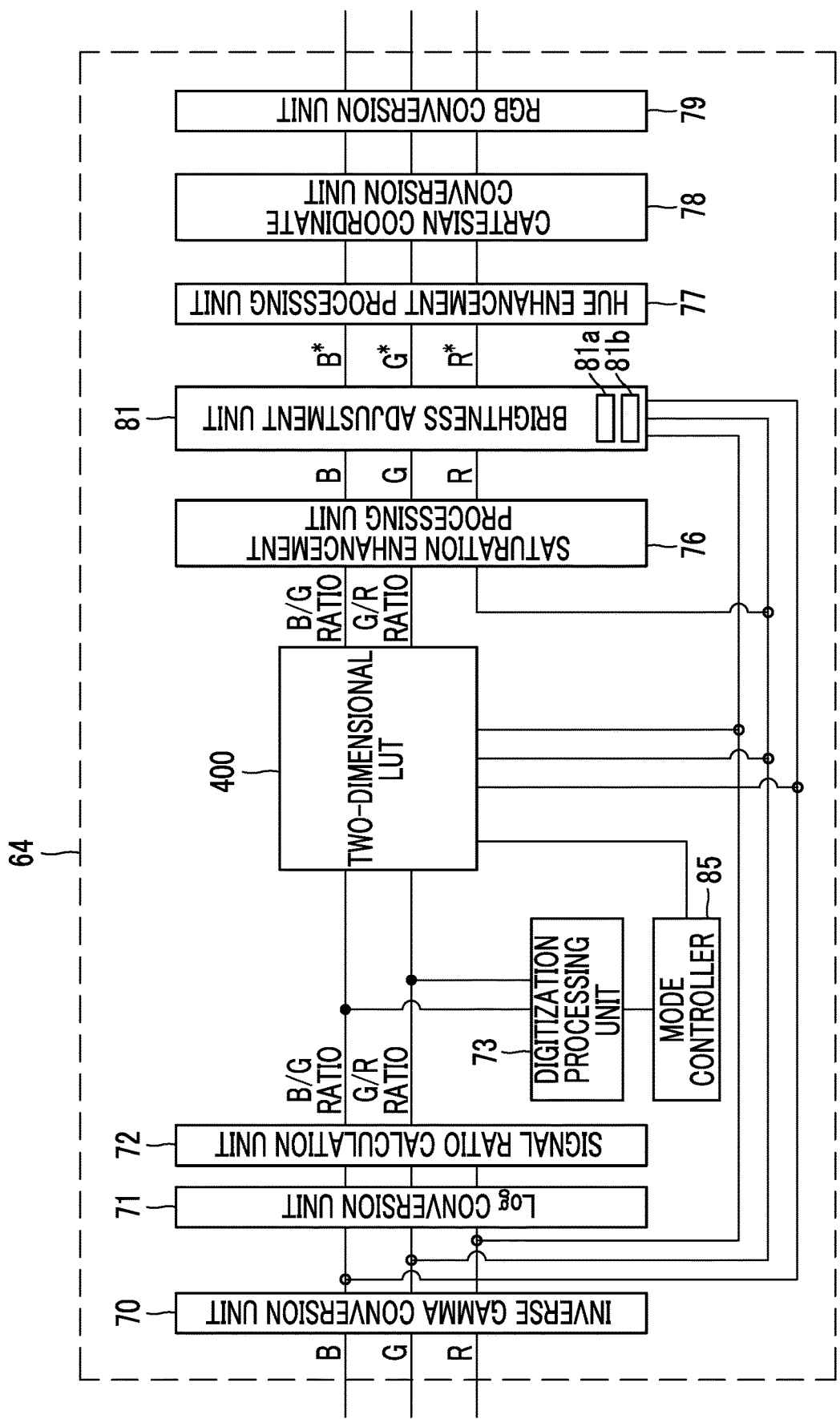
FIG. 35 is a block diagram showing functions of the special image processing unit in a case where a two-dimensional LUT is used.

In the first embodiment, although the B/G ratio and the G/R ratio are converted to the radius vector r and the deflection angle θ by polar coordinate conversion, the saturation enhancement processing and the hue enhancement processing for expanding or compressing are executed based on the radius vector r and the deflection angle θ after conversion, and thereafter, the radius vector r and the deflection angle θ are returned to the B/G ratio and the G/R ratio again, as shown in FIG. 35, the B/G ratio and the G/R ratio may be converted directly to the B/G ratio and the G/R ratio after the first or second processing using a two-dimensional look up table (LUT) 400 without performing polar coordinate conversion or the like.

In the two-dimensional LUT 400, the B/G ratio and the G/R ratio are stored in association with the B/G ratio and the G/R ratio subjected to the saturation enhancement processing and the hue enhancement processing obtained by executing the saturation enhancement processing and the hue enhancement processing based on the B/G ratio and the G/R ratio. In a case where the inflammation evaluation mode is set, the correspondence relationship between the B/G ratio and the G/R ratio and the B/G ratio and the G/R ratio subjected to the first saturation enhancement processing and the first hue enhancement processing is used. In a case where the UC screening mode is set, the correspondence relationship of the B/G ratio and the G/R ratio to the B/G ratio and the G/R ratio subjected to the second saturation enhancement processing and the second hue enhancement processing is used. The first RGB image signal output from the inverse gamma conversion unit 70 is input to the two-dimensional LUT 400 and the RGB conversion unit 79.

In the above-described embodiments, the hardware structures of processing units included in the processor device 16, such as an image signal input unit, a color information acquisition unit, a saturation enhancement processing unit, a hue enhancement processing unit, and a mode controller, are various processors described below. Various processors include a central processing unit (CPU) that is a general-purpose processor executing software (program) to function as various processing units, a programmable logic device (PLD) that is a processor capable of changing a circuit configuration after manufacture, such as a field programmable gate array (FPGA), a dedicated electric circuit that is a processor having a circuit configuration dedicatedly designed for executing specific processing, such as an application specific integrated circuit (ASIC), and the like.

One processing unit may be configured of one of various processors described above or may be configured of a combination of two or more processors (for example, a plurality of FPGAs or a combination of a CPU and an FPGA) of the same type or different types. A plurality of processing units may be configured of one processor. As an example where a plurality of processing units are configured of one processor, first, as represented by a computer, such as a client or a server, there is a form in which one processor is configured of a combination of one or more CPUs and software, and the processor functions as a plurality of processing units. Secondly, as represented by system on chip (SoC) or the like, there is a form in which a processor that implements all functions of a system including a plurality of processing units into one integrated circuit (IC) chip is used. In this way, various processing units may be configured using one or more processors among various processors described above as a hardware structure.

In addition, the hardware structure of various processors is, more specifically, an electric circuit (circuitry) in which circuit elements, such as semiconductor elements, are combined.

It should be noted that the invention can be applied to various medical image processing devices, in addition to the processor device incorporated in the endoscope system described in the first to third embodiments or the capsule endoscope system described in the fourth embodiment.

EXPLANATION OF REFERENCES

10: endoscope system
12: endoscope
12a: insertion portion
12b: operation portion
12c: bending portion
12d: tip portion
12e: angle knob
13a: mode selection SW
14: light source device
16: processor device
18: monitor
19: console (keyboard)
20a: V-LED
20b: B-LED
20c: G-LED
20d: R-LED 21: light source controller
23: optical path combination unit
30a: illumination optical system
30b: imaging optical system
41: light guide
45: illumination lens
46: objective lens
48: imaging sensor
50: CDS/AGC circuit
53: image signal input unit
56: DSP
58: noise elimination unit
60: signal switching unit
62: normal image processing unit
64: special image processing unit
66: video signal generation unit
70: inverse gamma conversion unit
71: Log conversion unit
72: signal ratio calculation unit
73: digitization processing unit
74: image processing switching unit
75: polar coordinate conversion unit
76: saturation enhancement processing unit
76: conversion unit
77: hue enhancement processing unit
78: Cartesian coordinate conversion unit
79: RGB conversion unit
81: brightness adjustment unit
81a: first brightness information calculation unit
81b: second brightness information calculation unit
82: structure enhancement unit
83: inverse Log conversion unit
84: gamma conversion unit
85: mode controller
86: brightness/color difference signal conversion unit
87: HSV conversion unit
92: special image processing unit
96: special image processing unit
100: endoscope system
104: blue laser beam source
106: blue-violet laser beam source
108: light source controller
110: phosphor
200: endoscope system
202: broadband light source
204: rotary filter
205: filter switching unit
206: imaging sensor
208: filter for normal observation mode
208a: B filter
208b: G filter
208c: R filter
209: filter for a special observation mode
209a: Bn filter
209b: G filter
209c: R filter
300: capsule endoscope system
302: capsule endoscope
302b: imaging sensor
302c: image processing unit
302d: transmission antenna
304: transmission/reception antenna
306: reception device for capsule
400: two-dimensional LUT

What is claimed is:

1. A medical image processing device comprising:
a processor configured to:
receive a color image signal as input;
acquire a plurality of pieces of color information from the color image signal; and
execute saturation enhancement processing on a high saturation range on a high saturation side with respect to a single specific saturation boundary line in a feature space formed from the plurality of pieces of color information to make differences in saturation among a plurality of observation target ranges distributed as an observation target large,
wherein the processor executes, as the saturation enhancement processing with respect to the single specific saturation boundary line, first saturation enhancement processing and second saturation enhancement processing different from the first saturation enhancement processing, and
the high saturation range after the second saturation enhancement processing is greater than the high saturation range after the first saturation enhancement processing, and a value included in the high saturation range after the second saturation enhancement processing is smaller than a value included in the high saturation range after the first saturation enhancement processing.

2. The medical image processing device according to claim 1, wherein the processor further configured to:
execute hue enhancement processing on a specific hue range in a specific hue direction with respect to at least a specific hue boundary line in the feature space to make differences in hue among a plurality of observation target ranges distributed as an observation target large,
wherein the processor executes, as the hue enhancement processing, first hue enhancement processing or second hue enhancement processing with the difference in hue greater than the first hue enhancement processing.

3. The medical image processing device according to claim 2, wherein the processor further configured to:
perform switching between a first mode for obtaining a first saturation enhanced image from a color image signal subjected to the first saturation enhancement processing and a second mode for obtaining a second saturation enhanced image from a color image signal subjected to the second saturation enhancement processing.

4. The medical image processing device according to claim 3,
wherein the processor automatically performs switching between the first mode and the second mode according to observation target information obtained by digitizing a state of the observation target.

5. The medical image processing device according to claim 4,
wherein the observation target information corresponds to a value obtained based on the color information of any one observation target range of the plurality of observation target ranges.

6. The medical image processing device according to claim 4,
wherein the observation target information corresponds to a value obtained based on an angle of coordinates of any one observation target range of the plurality of observation target ranges with respect to the specific hue boundary line.

7. The medical image processing device according to claim 4, wherein the observation target information corresponds to a value obtained based on a distance between two observation target ranges among the plurality of observation target ranges.

8. The medical image processing device according to claim 4,
wherein the observation target information is an area ratio indicating an occupying ratio of pixels of any one observation target range of the plurality of observation target ranges among pixels of the color image signal.

9. The medical image processing device according to claim 4,
wherein the observation target information is a degree of inflammation obtained by digitizing an inflamed state of the observation target.

10. The medical image processing device according to claim 1,
wherein the color image signal is obtained by imaging an observation target illuminated with illumination light including violet light.

11. An endoscope system comprising:
the medical image processing device according to claim 1; and
a display that displays at least one image of a first saturation enhanced image obtained from a color image signal subjected to the first saturation enhancement processing, a second saturation enhanced image obtained from a color image signal subjected to the second saturation enhancement processing, or a normal image obtained from a color image signal not subjected to the first saturation enhancement processing and the second saturation enhancement processing.

12. A method of operating a medical image processing device, the method comprising:
an image signal input step in which a color image signal is input to an image signal input unit;
a color information acquisition step in which a color information acquisition unit acquires a plurality of pieces of color information from the color image signal; and
a saturation enhancement processing step in which a saturation enhancement processing unit executes saturation enhancement processing on a high saturation range on a high saturation side with respect to a single specific saturation boundary line in a feature space formed from the plurality of pieces of color information to make differences in saturation among a plurality of observation target ranges distributed as an observation target large,
wherein, in the saturation enhancement processing step, as the saturation enhancement processing with respect to the single specific saturation boundary line, first saturation enhancement processing and second saturation enhancement processing different from the first saturation enhancement processing are executed, and
the high saturation range after the second saturation enhancement processing is greater than the high saturation range after the first saturation enhancement processing, and a value included in the high saturation range after the second saturation enhancement processing is smaller than a value included in the high saturation range after the first saturation enhancement processing.

* * * * *